(12) United States Patent
Rothberg et al.

(10) Patent No.: US 6,190,868 B1
(45) Date of Patent: Feb. 20, 2001

(54) METHOD FOR IDENTIFYING A NUCLEIC ACID SEQUENCE

(75) Inventors: Jonathan M. Rothberg, Guilford, CT (US); Michael W. Deem, Los Angeles, CA (US); John W. Simpson, Madison, CT (US)

(73) Assignee: CuraGen Corporation, New Haven, CT (US)

( * ) Notice: Under 35 U.S.C. 154(b), the term of this patent shall be extended for 0 days.

(21) Appl. No.: 09/381,779

(22) PCT Filed: Aug. 7, 1998

(86) PCT No.: PCT/US98/16548

§ 371 Date: Sep. 23, 1999

§ 102(e) Date: Sep. 23, 1999

(87) PCT Pub. No.: WO99/07896

PCT Pub. Date: Feb. 18, 1999

Related U.S. Application Data

(60) Provisional application No. 60/054,887, filed on Aug. 7, 1997.

(51) Int. Cl.[7] .............................. C12Q 1/68; C12P 19/34
(52) U.S. Cl. .............................................. 435/6; 435/91.2
(58) Field of Search ........................... 435/6, 91.2, 91.1; 536/24.1

(56) References Cited

U.S. PATENT DOCUMENTS

| 5,202,231 | 4/1993 | Drmanac et al. . |
| 5,459,037 | 10/1995 | Sutcliffe et al. . |

FOREIGN PATENT DOCUMENTS

| 0 534 858 A1 | 3/1993 | (EP) . |
| WO 97/15690 | 5/1997 | (WO) . |

OTHER PUBLICATIONS

Chevet, et al., 1995. "Low concentrations of tetramethylammonium chloride increase yield and specificity of PCR." Nucleic Acids Research. 23:3343–3344.

Drmanac, et al., 1993. "DNA sequence determination by hybridization: a strategy for efficient large–scale sequencing." Science. 260:1649–52.

Guo, et al., 1994. "Direct fluorescence analysis of genetic polymorphisms by hybridization with oligonucleotide arrays on glass supports." Nucleic Acid Research. 22:5456–65.

Ju, 1995. "Fluorescent energy transfer dye–labeled primers for DNA sequencing and analysis." Proc. Nati. Acad Sci. USA 92:4347–4351.

Lennon and Lehrach, 1991. "Hybridization analyses of arrayed cDNA libraries." Trends in Genetics. 12 7:314–317.

Liang, 1992. "Differential display of eukaryotic messenger RNA by means of the polymerase chain reaction." Science. 15 257:967–971.

Liang and Pardee, 1995. "Recent advances in differential display." Current Opinions in Immunology. 11 7:274–280.

Lisitsyn, et al., 1993. "Cloning the differences between two complex genomes." Science. 259:946–50.

Mutter and Boynton, 1995. "PCR bias in amplification of androgen receptor alleles, a trinucleotide repeat marker used in clonality studies." Nuc. Acid Res. 2 23:1411–1418.

Prashar, 1996. "Analysis of Differential Gene Expression by Display of 3'–end Restriction Fragments of cDNAs." Proc. Nat. Acad. Sci. USA. 3 93:659–663.

Welsh, et al., 1992. "Arbitrarily primed PCR fingerprinting of RNA." Nucleic Acid Res. 20:4965–70.

Shimkets, R. (1999). Gene expression analysis by transcript profiling coupled to a gene database query. *Nature Biotechnology*, 17:798–803.

*Primary Examiner*—John S. Brusca
*Assistant Examiner*—Young Kim
(74) *Attorney, Agent, or Firm*—Ivor R. Elrifi; Mintz, Levin, Cohn, Ferris, Glovsky and Popeo, P.C.

(57) ABSTRACT

The present invention discloses a methodology which is directed to providing positive confirmation that nucleic acids, possessing putatively identified sequence predicted to generate observed GeneCalling™ signals, are actually present within the sample from which the signal was originally derived. The putatively identified nucleic acid fragment within the sample possesses 3'- and 5'-ends with known terminal subsequences, said method comprising; contacting said nucleic acid fragments in said sample in amplifying conditions with (i) a nucleic acid polymerase; (ii) "regular" primer oligonucleotides having sequences comprising hybridizable portions of said known terminal subsequences; and (iii) a "poisoning" oligonucleotide primer, said poisoning primer having a sequence comprising a first subsequence that is a portion of the sequence of one of said known terminal subsequences and a second subsequence that is a hybridizable portion of said putatively unidentified sequence which is adjacent to said one known terminal subsequence, wherein nucleic acids amplified with said poisoning primer are distinguishable upon detection from nucleic acids amplified with said nucleic acids amplified only with said regular primers; separating the products of the contacting step; and the detecting sequence is confirmed if the nucleic acids amplified with said poisoning primer are detected.

14 Claims, 6 Drawing Sheets

- HOMO SAPIENS, 2493 bp (RNA).
GENE SEQUENCE
```
   1 ggatcgattt gagtaagagc atagctgtcg ggagagccca ggattcaaca cgggccttga
  61 gaaatgtggc tcttgtacct cctggtgccg gccctgttct gcagggcagg aggctccatt
 121 cccatccctc agaagttatt tggggaggtg acttcccctc tgttccccaa gccttacccc
 181 aacaactttg aaacaaccac tgtgatcaca gtccccacgg gatacagggt gaagctcgtc
 241 ttccagcagt ttgacctgga gccttctgaa ggctgcttct atgattatgt caagatctct
 301 gctgataaga aaagcctggg gaggttctgt gggcaactgg gttctccact gggcaacccc
 361 ccgggaaaga aggaatttat gtcccaaggg aacaagatgc tgctgacctt ccacacagac
 421 ttctccaacg aggagaatgg gaccatcatg ttctacaagg gcttcctggc ctactaccaa
 481 gctgtggacc ttgatgaatg tgcttcccgg agcaaatcag gggaggagga tccccagccc
 541 cagtgccagc acctgtgtca caactacgtt ggaggctact tctgttcctg ccgtccaggc
 601 tatgagcttc aggaagacag gcattcctgc caggctgagt gcagcagcga gctgtacacg
 661 gaggcatcag gctacatctc cagcctggag taccctcggt cctacccccc tgacctgcgc
 721 tgcaactaca gcatccgggt ggagcggggc ctcaccctgc acctcaagtt cctggagcct
 781 tttgatattg atgaccacca gcaagtacac tgcccctatg accagctaca gatctatgcc
 841 aacgggaaga acattggcga gttctgtggg aagcaaaggc cccccgacct cgacaccagc
 901 agcaatgctg tggatctgct gttcttcaca gatgagtcgg gggacagccg gggctggaag
 961 ctgcgctaca ccaccgagat catcaagtgc ccccagccca agaccctaga cgagttcacc
1021 atcatccaga acctgcagcc tcagtaccag ttccgtgact acttcattgc tacctgcaag
1081 caaggctacc agctcataga ggggaaccag gtgctgcatt ccttcacagc tgtctgccag
1141 gatgatggca cgtggcatcg tgccatgccc agatgcaaga tcaaggactg tgggcagccc
1201 cgaaacctgc ctaatggtga cttccgttac accaccacaa tgggagtgaa cacctacaag
1261 gcccgtatcc agtactactg ccatgagcca tattacaaga tgcagaccag agctggcagc
1321 agggagtctg agcaagggt gtacacctgc acagcacagg catttggaa gaatgaacag
1381 aagggagaga agattcctcg gtgcttgcca gtgtgtggga gcccgtgaa ccccgtggaa
1441 cagaggcagc gcataatcgg agggcaaaaa gccaagatgg gcaacttccc ctggcaggtg
1501 ttcaccaaca tccacgggcg cggggcggg gccctgctgg gcgaccgctg gatcctcaca
1561 gctgcccaca ccctgtatcc caaggaacac gaagcgcaaa gcaacgcctc tttggatgtg
1621 ttcctgggcc acacaaatgt ggaagagctc atgaagctag gaaatcaccc catccgcagg
1681 gtcagcgtcc acccggacta ccgtcaggat gagtcctaca attttgaggg ggacatcgcc
1741 ctgctggagc tggaaaatag tgtcaccctg ggtcccaacc tcctccccat ctgcctccct
1801 gacaacgata ccttctacga cctgggcttg atgggctatg tcagtggctt cggggtcatg
1861 gaggagaaga ttgctcatga cctcaggttt gtccgtctgc ccgtagctaa tccacaggcc
1921 tgtgagaact ggctccgggg aaagaatagg atggatgtgt ctctcaaaa catgttctgt
1981 gctggacacc catctctaaa gcaggacgcc tgccaggggg atagtggggg cgttttgca
2041 gtaagggacc cgaacactga tcgctgggtg gccacgggca tgtgtcctg gggcatcggg
2101 tgcagcaggg gctatggctt ctacaccaaa gtgctcaact acgtggactg gatcaagaaa
2161 gagatggagg aggaggactg agcccagaat tcactaggtt cgaatccaga gagcagtgtg
2221 gaaaaaaaaa aaacaaaaaa caactgacca gttgttgata accactaaga gtctctatta
2281 aaattactga tgcagaaaga ccgtgtgtga aattctcttt cctgtagtcc cattgatgta
2341 ctttacctga acaacccaa aggccccttt ctttcttctg aggattgcag aggatatagt
2401 tatcaatctc tagttgtcac tttcctcttc cactttgata ccattgggtc attgaatata
2461 acttttccca aataagttt tatgagaaat gc
```

Fig. 4

SEQUENCE LISTING

<160> NUMBER OF SEQ ID NOS: 5

<210> SEQ ID NO 1
<211> LENGTH: 2492
<212> TYPE: DNA
<213> ORGANISM: Homo sapiens

<400> SEQUENCE: 1

```
ggatcgattt gagtaagagc atagctgtcg ggagagccca ggattcaaca cgggccttga      60
gaaatgtggc tcttgtacct cctggtgccg gccctgttct gcagggcagg aggctccatt     120
cccatccctc agaagttatt tggggaggtg acttcccctc tgttccccaa gccttacccc     180
aacaactttg aaacaaccac tgtgatcaca gtccccacgg gatacagggt gaagctcgtc     240
ttccagcagt ttgacctgga gccttctgaa ggctgcttct atgattatgt caagatctct     300
gctgataaga aagcctggg gaggttctgt gggcaactgg gttctccact gggcaacccc     360
ccgggaaaga aggaatttat gtcccaaggg aacaagatgc tgctgacctt ccacacagac     420
ttctccaacg aggagaatgg gaccatcatg ttctacaagg gcttcctggc ctactaccaa     480
gctgtggacc ttgatgaatg tgcttcccgg agcaaatcag gggaggagga tccccagccc     540
cagtgccagc acctgtgtca caactacgtt ggaggctact tctgttcctg ccgtccaggc     600
tatgagcttc aggaagacag gcattcctgc caggctgagt gcagcagcga gctgtacacg     660
gaggcatcag gctacatctc cagcctggag taccctcggt cctacccccc tgacctgcgc     720
tgcaactaca gcatccgggt ggagcgggc ctcaccctgc acctcaagtt cctggagcct     780
tttgatattg atgaccacca gcaagtacac tgcccctatg accagctaca gatctatgcc     840
aacgggaaga acattggcga gttctgtggg aagcaaaggc cccccgacct cgacaccagc     900
agcaatgctg tggatctgct gttcttcaca gatgagtcgg gggacagccg gggctggaag     960
ctgcgctaca ccaccgagat catcaagtgc ccccagccca gaccctaga cgagttcacc    1020
atcatccaga acctgcagcc tcagtaccag ttccgtgact acttcattgc tacctgcaag    1080
caaggctacc agctcataga ggggaaccag gtgctgcatt ccttcacagc tgtctgccag    1140
gatgatggca cgtggcatcg tgccatgccc agatgcaaga tcaaggactg tgggcagccc    1200
cgaaacctgc ctaatggtga cttccgttac accaccacaa tgggagtgaa cacctacaag    1260
gcccgtatcc agtactactg ccatgagcca tattacaaga tgcagaccag agctggcagc    1320
agggagtctg agcaagggt gtacacctgc acagcacagg gcatttggaa gaatgaacag    1380
aagggagaga agattcctcg gtgcttgcca gtgtgtggga gcccgtgaa ccccgtggaa    1440
cagaggcagc gcataatcgg agggcaaaaa gccaagatgc gcaacttccc ctggcaggtg    1500
ttcaccaaca tccacgggcg cggggcggg gccctgctgg gcgaccgctg gatcctcaca    1560
gctgcccaca ccctgtatcc caaggaacac gaagcgcaaa gcaacgcctc tttggatgtg    1620
ttcctgggcc acacaaatgt ggaagagctc atgaagctag gaaatcaccc catccgcagg    1680
gtcagcgtcc acccggacta ccgtcaggat gagtcctaca attttgaggg ggacatcgcc    1740
ctgctggagc tggaaaatag tgtcacccctg gtcccaacc tcctccccat ctgcctccct    1800
gacaacgata ccttctacga cctgggcttg atgggctatg tcagtggctt cggggtcatg    1860
```

-continued

```
gaggagaaga ttgctcatga cctcaggttt gtccgtctgc ccgtagctaa tccacaggcc    1920
tgtgagaact ggctccgggg aaagaatagg atggatgtgt tctctcaaaa catgttctgt    1980
gctggacacc catctctaaa gcaggacgcc tgccaggggg atagtggggg cgttttttgca   2040 gtaagggacc cgaacactga tcgctgggtg gccacgggca tcgtgtcctg gggcatcggg    2100
tgcagcaggg gctatggctt ctacaccaaa gtgctcaact acgtggactg gatcaagaaa    2160
gagatggagg aggaggactg agcccagaat tcactaggtt cgaatccaga gagcagtgtg    2220
gaaaaaaaaa aaacaaaaaa caactgacca gttgttgata accactaaga gtctctatta    2280
aaattactga tgcagaaaga ccgtgtgtga aattctcttt cctgtagtcc cattgatgta    2340
ctttacctga acaacccaa aggccccttt ctttcttctg aggattgcag aggatatagt    2400
tatcaatctc tagttgtcac tttcctcttc cactttgata ccattgggtc attgaatata    2460 acttttttcca aataaagttt tatgagaaat gc                                 2492
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: J primer

<400> SEQUENCE: 2
accgacgtcg actatccatg aaga                                           24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: R primer

<400> SEQUENCE: 3
agcactctcc agcctctcac cgaa                                           24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: poison J
      primer

<400> SEQUENCE: 4
tgaagacatg acctcaggtt tg                                             22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: poison R
      primer

<400> SEQUENCE: 5
accgaaaatt ctgggctcag tc                                             22

METHOD FOR IDENTIFYING A NUCLEIC ACID SEQUENCE

RELATED APPLICATIONS AND GRANT SUPPORT

This application claims priority to U.S. Provisional Patent Application Ser. No. 60/054,887 originally filed on Aug. 7, 1997, which is entitled "METHOD AND APPARATUS FOR IDENTIFYING, QUANTIFYING, AND CONFIRMING DNA SEQUENCES IN A SAMPLE WITHOUT SEQUENCING" and is hereby incorporated in its entirety by reference herein.

The invention disclosed herein was made utilizing United States Government support under Grant Number 70NANB5H1036 awarded by the National Institute of Standards and Technology. Accordingly, the United States Government has certain rights in the invention.

FIELD OF THE INVENTION

The field of the invention is DNA sequence classification, identification or determination, and quantification; more particularly it is the quantitative classification, comparison of expression, or identification of preferably all DNA sequences or genes in a sample without performing any associated sequencing.

BACKGROUND OF THE INVENTION

As molecular biological and genetics research have advanced, it has become increasingly clear that the temporal and spatial expression of genes plays a vital role in processes occurring in both health and in disease. Moreover, the field of biology has progressed from an understanding of how single genetic defects cause the traditionally recognized hereditary disorders (e.g., the thalassemias), to a realization of the importance of the interaction of multiple genetic defects in concert with various environmental factors in the etiology of the majority of the more complex disorders, such as neoplasia.

For example, in the case of neoplasia, recent experimental evidence has demonstrated the key causative roles of multiple defects in several pivotal genes causing their altered expression. Other complex diseases have been shown to have a similar etiology. Therefore, the more complete and reliable a correlation which can be established between gene expression and disease states, the better diseases will be able to be recognized, diagnosed and treated. This important correlation may be established by the quantitative determination and classification of DNA expression in tissue samples.

Genomic DNA ("gDNA") sequences are those naturally occurring DNA sequences constituting the genome of a cell. The overall state of gene expression within genomic DNA ("gDNA") at any given time is represented by the composition of cellular messenger RNA ("mRNA"), which is synthesized by the regulated transcription of gDNA. Complementary DNA ("cDNA") sequences may be synthesized by the process of reverse transcription of mRNA by use of viral reverse transcriptase. cDNA derived from cellular mRNA also represents, albeit approximately, gDNA expression within a cell at a given time. Accordingly, a methodology which would allow the rapid, economical and highly quantitative detection of all the DNA sequences within particular cDNA or gDNA samples is extremely desirable.

Heretofore, gene-specific DNA analysis methodologies have not been directed to the determination or classification of substantially all genes within a DNA sample representing the total transcribed cellular mRNA population and have universally required some degree of nucleic acid sequencing to be performed. As a result, existing cDNA and gDNA, analysis techniques have been directed to the determination and analysis of only one or two known or unknown genetic sequences at a single time. These techniques have typically utilized probes which are synthesized to specifically recognize (by the process of hybridization) only one particular DNA sequence or gene. See e.g., Watson, J. 1992. *Recombinant DNA*, chap 7, (W. H. Freeman, New York.). Furthermore, the adaptation of these methods to the recognition of all sequences within a sample would be, at best, highly cumbersome and uneconomical.

One existing method for detecting, isolating and sequencing unknown genes utilizes an arrayed cDNA library. From a particular tissue or specimen, mRNA is isolated and cloned into an appropriate vector, which is introduced into bacteria (e.g., *E. coli*) through the process of transformation. The transformed bacteria are then plated in a manner such that the progeny of individual vectors bearing the clone of a single cDNA sequence can be separately identified. A filter "replica" of such a plate is then probed (often with a labeled DNA oligomer selected to hybridize with the cDNA representing the gene of interest) and those bacteria colonies bearing the cDNA of interest are identified and isolated. The cDNA is then extracted and the inserts contained therein is subjected to sequencing via protocols which includes, but are not limited to the dideoxynucleotide chain termination method. See Sanger, F., et al. 1977. DNA Sequencing with Chain Terminating Inhibitors. Proc. Natl. Acad. Sci. USA 74(12):5463–5467.

The oligonucleotide probes utilized in colony selection protocols for unknown gene(s) are synthesized to hybridize, preferably, only with the cDNA for the gene of interest. One method of achieving this specificity is to start with the protein product of the gene of interest. If a partial sequence (i.e., from a peptide fragment containing 5 to 10 amino acid residues) from an active region of the protein of interest can be determined, a corresponding 15 to 30 nucleotide (nt.) degenerate oligonucleotide can be synthesized which would code for this peptide fragment. Thus, a collection of degenerate oligonucleotides will typically be sufficient to uniquely identify the corresponding gene. Similarly, any information leading to 15–30 nt. subsequences can be used to create a single gene probe.

Another existing method, which searches for a known gene in cDNA or gDNA prepared from a tissue sample, also uses single-gene or single-sequence oligonucleotide probes which are complementary to unique subsequences of the already known gene sequences. For example, the expression of a particular oncogene in sample can be determined by probing tissue-derived cDNA with a probe which is derived from a subsequence of the oncogene's expressed sequence tag. The presence of a rare or difficult to culture pathogen (e.g., the TB bacillus) can also be determined by probing gDNA with a hybridization probe specific to a gene possessed by the pathogen. Similarly, the heterozygous presence of a mutant allele in a phenotypically normal individual, or its homozygous presence in a fetus, may be determined by the utilization of an allele-specific probe which is complementary only to the mutant allele. See e.g., Guo, N. C., et al. 1994. *Nucleic Acid Research* 22:5456–5465).

Currently, all of the existing methodologies which utilize single-gene probes, if applied to determine all of the genes expressed within a given tissue sample, would require many thousands to tens-of-thousands of individual probes. It has been estimated that a single human cell typically expresses approximately 5,000 to 15,000 genes simultaneously, and that the most complex types of tissues (e.g., brain tissue) can express up to one-half of the total genes contained within the human genome. See Liang, et al. 1992. Differential Display of Eukaryotic Messenger RNA by Means of the Polymerase Chain Reaction. *Science* 257:967–971. It is obvious that an screening methodology which requires such a large number of probes is clearly far too cumbersome to be economic or, even practical.

In contrast, another class of existing methods, known as sequencing-by-hybridization ("SBH"), utilize combinatorial probes which are not gene specific. See e.g., Drmanac, et al. 1993. *Science* 260:1649–1652; U.S. Pat. No. 5,202,231 to Drmanac, et al. An exemplar implementation of SBH for the determination of an unknown gene requires that a single cDNA clone be probed with all DNA oligomers of a given length, say, for example, all 6 nt. oligomers. A set of oligomers of a given length which are synthesized without any type of selection is called a combinatorial probe library. A partial DNA sequence for the cDNA clone can be reconstructed by algorithmic manipulations from the hybridization results for a given combinatorial library (i.e., the hybridization results for the 4096 oligomer probes having a length of 6 nt.). However, complete nucleotide sequences are not determinable, because the repeated subsequences cannot be fully ascertained in a quantitative manner.

SBH which is adapted to the identification of known genes is called oligomer sequence signatures ("OSS"). See e.g., Lennon, et al. 1991. *Trends In Genetics* 7(10:314–317. OSS classifies a single clone based upon the pattern of probe "hits" (i.e., hybridizations) against an entire combinatorial library, or a significant sub-library. This methodology requires that the tissue sample library be arrayed into clones, wherein each clone comprises only a single sequence from the library. This technique cannot be applied to mixtures of sequences.

These previous, exemplar methodologies are all directed to finding one sequence in an array of clones—with each clone expressing a single sequence from a given tissue sample. Accordingly, they are not directed to rapid, economical, quantitative, and precise characterization of all the DNA sequences in a mixture of sequences, such as a particular total cellular cDNA or gDNA sample, and their adaptation to such a task would be prohibitive. Determination by sequencing the DNA of a clone, much less an entire sample of thousands of genomic sequences, is not rapid or inexpensive enough for economical and useful diagnostics. As previously discussed, existing probe-based techniques of gene determination or classification, whether the genes are known or unknown, require many thousands of probes, each specific to one possible gene to be observed, or at least thousands or even tens of thousands of probes in a combinatorial library. Further, all of these aforementioned methods require the sample be arrayed into clones each expressing a single gene of the sample.

In contrast to the prior exemplar gene determination and classification techniques, another methodology, known as differential display, attempts to "fingerprint" a mixture of expressed genes, as is found in a pooled cDNA library. This "fingerprint," however, seeks merely to establish whether two samples are the same or different. No attempt is made to determine the quantitative, or even qualitative, expression of particular genes. See e.g., Liang, et al. 1995. *Curr. Opin. Immunol.* 7:274–280; Liang, et al. 1992. *Science* 257:967–971; Welsh, et al. 1992. *Nuc. Acid Res.* 20:4965–4970; McClelland, et al. 1993. *Exs.* 67:103–115 and Lisitsyn, 1993. *Science* 259:946–950. Differential display uses the polymerase chain reaction ("PCR") to amplify DNA subsequences of various lengths, which are then defined by their being between the annealing sites of arbitrarily selected primers. Polymerase chain reaction method and apparatus are well known. See, e.g., U.S. Pat. Nos. 4,683,202; 4,683,195; 4,965,188; 5,333,675; each herein fully incorporated by reference. Ideally, the pattern of the lengths observed is characteristic of the specific tissue from which the library was originally prepared. Typically, one of the primers utilized in differential display is oligo(dT) and the other is one or more arbitrary oligonucleotides which are designed to hybridize within a few hundred base pairs (bp.) of the homopolymeric poly-dA tail of a cDNA within the library. Thereby, upon electrophoretic separation, the amplified fragments of lengths up to a few hundred base pairs should generate bands which are characteristic and distinctive of the sample. In addition, changes in gene expression within the tissue may be observed as changes in one or more of the cDNA bands.

In the differential expression methodology, although characteristic electrophoretic banding patterns develop, no attempt is made to quantitatively "link" these patterns to the expression of particular genes. Similarly, the second arbitrary primer also cannot be traced to a particular gene due to the following reasons. First, the PCR process is less than ideally specific. One to several base pair mismatches are permitted by the lower stringency annealing step which is typically utilized in this methodology and are generally tolerated well enough so that a new chain can actually be initiated by the Taq polymerase often used in PCR reactions. Secondly, the location of a single subsequence (or its absence) is insufficient to distinguish all expressed genes. Third, the resultant bp.-length information (i.e., from the arbitrary primer to the poly-dA tail) is generally not found to be characteristic of a sequence due to: (i) variations in the processing of the 3'-untranslated regions of genes, (ii) variation in the poly-adenylation process and (iii) variability in priming to the repetitive sequence at a precise point. Therefore, even the bands which are produced often are smeared by numerous, non-specific background sequences.

Moreover, known PCR biases towards nucleic acid sequences containing high G+C content and short sequences, further limit the specificity of this methodology. In accord, this technique is generally limited to the "fingerprinting" of samples for a similarity or dissimilarity determination and is precluded from use in quantitative determination of the differential expression of identifiable genes.

Thus, in conclusion, the existing methodologies utilized for gene or DNA sequence classification and determination are in need of improvement with respect to their ability to perform a highly specific quantitative determination of the components of a cDNA mixture prepared from a tissue sample in a rapid, economical and reproducible manner.

SUMMARY OF THE INVENTION

The preferred embodiment of the present invention discloses a methodology which is directed to providing positive confirmation that nucleic acid fragments, possessing putatively identified sequences which have been predicted to generate observed signals generated according to the methods described in PCT Publication WO 97/15690 (referred to herein as "GeneCalling™", claiming priority to now issued U.S. Pat. No. 5,871,697, incorporated herein by reference in its entirety), are actually present within the sample generating the signal. This methodology, hereinafter known as "oligo-poisoning," confirms the presence of a specific, defined flanking nucleic acid subsequence which is adjacent to the "target" subsequence of interest recognized by the probing means within a nucleic acid-containing sample. Oligo-poisoning proceeds by initially performing PCR amplification of, for example GeneCalling™ reaction products, so as to produce results which indicate whether a nucleic acid fragment contained within the GeneCalling™ reaction either possesses or lacks the putatively identified subsequence. In the preferred embodiment, this is achieved by adding a molar excess of a "poisoning" primer designed to amplify only those nucleic acid fragments having the putatively identified subsequence. The "poisoning" primer may, preferably, be unlabeled or it may be labeled so as to allow it to be differentiated from any other type of label utilized in the PCR amplification reaction. Following PCR amplification, the resulting reaction products are then separated by electrophoresis. As those nucleic acid fragments containing the putatively identified subsequence which have undergone amplification will be, preferably, unlabeled, they will not generate a detectable signal. Accordingly, all amplification products of such nucleic acid fragments will be unlabeled and undetectable.

Importantly, oligo-poisoning is also equally applicable to confirming putative sequence identifications in any sample, of nucleic acid fragments which possess a certain generic sequence structure or motif. This generic structure only limits fragments to have known terminal subsequences capable of acting as PCR primers. Several methods are known in the art for producing samples with such a generic structure.

The present invention provides a methodology for confirming a putatively identified sequence of a nucleic acid fragment in a sample of nucleic acids wherein each nucleic acid fragment within said sample possesses known, 3'- and 5'-terminal subsequences, said methodology comprising; contacting said nucleic acid fragments in said sample in amplifying conditions with (i) a nucleic acid polymerase; (ii) "regular" primer oligonucleotides having sequences comprising hybridizable portions of said known terminal subsequences; and (iii) a "poisoning" oligonucleotide primer, said "poisoning" primer having a sequence comprising a first subsequence that is a portion of the sequence of one of said known terminal subsequences and a second subsequence that is a hybridizable portion of said putatively unidentified sequence which is adjacent to said one known terminal subsequence, wherein nucleic acids amplified with said "poisoning" primer are distinguishable upon detection from nucleic acids amplified with said nucleic acids amplified only with said regular primers; separating the products of the contacting step; and the detecting sequence is confirmed if the nucleic acids amplified with said "poisoning" primer are detected.

The present invention further provides that: (i) the regular PCR primers are labeled and, preferably, said "poisoning" primer is unlabeled; (ii) the regular PCR primers are labeled and the "poisoning" primer is labeled in a detectably different manner so as to allow its differentiation from any other label utilized in the amplification reaction; or (iii) the regular PCR primers are unlabeled and the poisoning primer is labeled and, optionally, wherein the step of detecting said separated products further comprises confirming said putatively identified sequence if said nucleic acid fragment with a putatively identified sequence is not detected. In the preferred embodiment of the present invention the regular PCR primers are labeled and, preferably, said "poisoning" primer is unlabeled.

It is an object of this invention to provide a methodology for the rapid, economical, quantitative, and highly specific determination or classification of DNA sequences, in particular genomic DNA (gDNA) or complementary DNA (cDNA) sequences, in either arrays of single sequence clones or mixtures of sequences such as can be derived from tissue samples, without actually sequencing the DNA. Thereby, the aforementioned deficiencies within the background arts are greatly mitigated. This objective is realized by generating a plurality of distinctive and detectable signals from the DNA sequences in the sample being analyzed. Preferably, all the resultant signals taken together have sufficient discrimination and resolution so that each particular DNA sequence contained within a sample may be individually classified by the particular signals it generates, and with reference to a database of all DNA sequences possible in the sample, individually determined. The intensity of the signals indicative of a particular DNA sequence depends, preferably, on the amount of that DNA present. Alternatively, the signals together can classify a predominant fraction of the DNA sequences into a plurality of sets of approximately no more than two to four individual sequences.

It is a further object that the numerous signals be generated from measurements of the results of as few a number of recognition reactions as possible, preferably no more than approximately 5–400 reactions, and most preferably no more than approximately 20–200 reactions. It should be noted that rapid and economical determinations would not be achieved if each DNA sequence in a sample containing a complex mixture required a separate reaction with a unique probe. Preferably, each recognition reaction generates a large number of or a distinctive pattern of distinguishable signals, which are quantitatively proportional to the amount of the particular DNA sequences present. Further, the signals are preferably detected and measured with a minimum number of observations, which are preferably capable of being simultaneously performed.

The signals are preferably optical in nature (e.g., generated by fluorochrome labels) and are, preferably, detected by automated optical detection technologies. Using these methods, multiple individually labeled moieties can be discriminated even though they are spatially located within the same "spot" on a hybridization membrane or electrophoretic gel band. Therefore, this level of discrimination permits multiplexing reactions and parallelizing signal detection. Alternatively, the invention is easily adaptable to other labeling systems (e.g., silver staining of gels). In particular, any single molecule detection system, whether optical or by some other technology (such as scanning or tunneling microscopy), would be highly advantageous for utilization according to this invention, as it would greatly improve the quantitative characteristics.

Signals (also referred to herein as "hits") are generated by detecting the presence or absence of short DNA subsequences (hereinafter called "target" subsequences) within a nucleic acid sequence of the sample to be subsequently analyzed. The presence or absence of a given subsequence is detected by use of recognition means (i.e., probes) for the subsequence. The subsequence(s) are recognized by various recognition means, including but not limited to restriction endonucleases ("REs"), DNA oligomers, and PNA oligomers. REs recognize their specific subsequences by cleavage thereof; DNA and PNA oligomers recognize their specific subsequences by hybridization methods. The preferred embodiment detects not only the presence of pairs of hits in a sample sequence but also include a representation of the length in base pairs between adjacent hits. This length representation may be corrected to true physical length in base pairs upon the removal of experimental biases and errors inherent in the length separation and detection means. An alternative embodiment detects only the pattern of hits in an array of clones, each containing a single sequence ("single sequence clones"). This may be accomplished by knowing the sequence of each clone and/or by determining the length (either measured or physical) of the recognized sequences.

The generated signals are then analyzed together with DNA sequence information stored within sequence databases utilizing computer implemented experimental analysis methods to: (i) identify individual genes and (ii) establish their quantitative presence within the sample. The target subsequences are chosen by further computer implemented experimental design methods of the present invention such that their presence or absence, as well as their relative distances when present, yield a maximum amount of information for classifying or determining the DNA sequences to be analyzed.

By use of this methodology, it is possible to have orders of magnitude fewer probes than there are DNA sequences to be analyzed, and it is further possible to have considerably fewer probes than would be present in combinatorial libraries of the same length as the probes used in this invention. The target subsequences have a preferred probability of occurrence in a sequence (typically between 5% and 50%). In the preferred embodiment, it is preferred that the presence of one probe in a DNA sequence to be analyzed is independent of the presence of any other probe. Preferably, target subsequences are chosen based on information in relevant DNA sequence databases that characterize the sample. A minimum number of target subsequences may be chosen to determine the expression of all genes in a tissue sample (hereinafter "tissue mode"). Alternatively, a smaller number of target subsequences may be chosen to quantitatively classify or determine only one or a few sequences of genes of interest, for example oncogenes, tumor suppressor genes, growth factors, cell, cycle genes, cytoskeletal genes, and the like (hereinafter "query mode").

The preferred embodiment of this detection methodology, quantitative expression analysis (hereinafter referred to as "GeneCalling™") generates signals which comprise both the target subsequence presence and a representation of the length in base pairs between adjacent target subsequences via the measurement of the results of recognition reactions on cDNA (or gDNA) mixtures. A detailed disclosure of the GeneCalling™ methodology may be found in PCT/US96/17159, published as WO97/15690, herein incorporated by reference, which is entitled "METHOD AND APPARATUS FOR IDENTIFYING, QUANTIFYING, AND CONFIRMING DNA SEQUENCES IN A SAMPLE WITHOUT SEQUENCING." Most importantly, this methodology does not require the insertion of the cDNA into a vector so as to create individual clones in a library. It is well known within the relevant fields that the creation of these cDNA libraries is time consuming, costly, and introduces bias into the process, as it requires the cDNA in the vector to be transformed into bacteria, the bacteria arrayed as clonal colonies, and finally the growth of the individual transformed colonies.

As is disclosed in WO97/15690, three exemplar experimental methodologies may be utilized for GeneCalling™: (i) a preferred Polymerase Chain Reaction (PCR) based method; (ii) an RE/ligase/amplification procedure and (iii) a method utilizing a removal means, preferably biotin, for removal of unwanted DNA fragments. However, only the preferred PCR-based experimental methodology will be disclosed herein as it serves to generate precise, reproducible, noise free signatures for determining individual gene expression from DNA in mixtures or libraries and is uniquely adaptable to automation, as it does not require intermediate extractions or buffer exchanges. A computer implemented gene calling step uses the hit and length information measured in conjunction with a database of DNA sequences to determine which genes are present in the sample and the relative levels of expression. Signal intensities are used to determine relative amounts of sequences in the sample; whereas computer-implemented design methods optimize the choice of the target subsequences.

As previously discussed, the PCR-based GeneCalling™ methodology disclosed herein, preferably generates measurements that are precise, reproducible, and free of noise. Measurement noise in GeneCalling™ is typically created by generation or amplification of unwanted DNA fragments, and special steps are preferably taken to avoid any such unwanted fragments. This embodiment of the invention facilitates efficient analysis by permitting multiple recognition means to be tested in one reaction and by utilizing multiple, distinguishable labeling of the recognition means, so that signals may be simultaneously detected and measured. Preferably, for GeneCalling,™ labeling is accomplished by use of multiple fluorochrome moieties. An increase in sensitivity as well as an increase in the number of resolvable fluorescent labels can be achieved by the use of fluorescent, energy transfer, dye-labeled primers. Other detection methods, preferable when the genes being identified will be physically isolated from the gel for later sequencing or use as experimental probes, include the use of silver staining gels or of radioactive labeling. Since these methods do not allow for multiple samples to be run in a single lane, they are less preferable when high throughput is needed.

Due to the fact that the confirmation of GeneCalling™ by the oligo-poisoning methodology achieves rapid and economical quantitative determination and confirmation of differential gene expression in tissue or other samples, it has considerable medical and research utility. For example, in clinical medicine, as more and more diseases are recognized to have important genetic components to their etiology and development, it is becoming increasingly useful to be able to assay the genetic makeup and expression of a tissue sample. More specifically, the presence and expression of certain genes or their particular alleles are prognostic or risk factors for disease (including disorders). Several examples of such diseases are found among the neurodegenerative diseases, such as Huntington's disease and ataxia-telangiectasia. Several cancers (e.g., neuroblastoma) can now be quantitatively linked to specific genetic defects. Finally, gene expression can also determine the presence and classification of those foreign pathogens which are difficult or impossible to culture in vitro but which nevertheless express their own unique genes.

Similarly, disease progression is reflected in changes in genetic expression of an affected tissue. For example, expression of particular tumor promoter genes and lack of expression of particular tumor suppressor genes is now known to correlate with the progression of certain tumors from normal tissue, to hyperplasia, to cancer in situ, and finally, to metastatic cancer. The return of a cell population to a "normal" pattern of gene expression (e.g., through the use of anti-sense oligonucleotide technology), can correlate with tumor regression. The quantification of gene expression in a cancerous tissue can assist in staging and classifying this disease, as well as providing a basis to chose and guide therapy. Accurate disease classification and taging or grading using gene expression information can assist in choosing initial therapies that are increasingly more precisely tailored to the precise disease process occurring in the particular patient. Gene expression information can then track disease progression or regression, and such information can assist in monitoring the success or changing the course of an initial therapy. A favored therapy is one which results in a regression of an abnormal pattern of gene expression in an individual towards "normality," while a therapy which has little effect on gene expression (i.e., its abnormal progression) may be modified or discontinued. Such monitoring of gene expression is now useful for cancers and will become useful for an increasing number of other diseases, such as diabetes and obesity.

In order to facilitate the utilization of the present invention for the quantitative detection, confirmation and monitoring of such differential gene expression in patients with the aforementioned diseases, it is envisioned that the GeneCalling™/oligo-poisoning methodologies will be incorporated into a unitized "kit" form. This will enable the researcher or health care provider to rapidly and accurately assess such differential gene expression in the most efficacious manner possible. For example, the kit may utilize non-radioactive labeling of the PCR amplification probes and "pre-cast" electrophoresis gels to ameliorate some of the difficulties indigenous to these methodologies, thus markedly increasing the potential for the acceptance and widespread use of such a kit in less sophisticated settings (i.e., a physician's office).

Furthermore, in the case of direct gene therapy, expression analysis directly monitors the success of treatment. In biological research, rapid and economical assay for gene expression in tissue or other samples has numerous applications. Such applications include, but are not limited to, for example, in pathology examining tissue specific genetic response to disease, in embryology determining developmental changes in gene expression, in pharmacology assessing direct and indirect effects of drugs on gene expression. In these applications, this invention can be applied, for example, to in vitro cell populations or cell lines, to in vivo animal models of disease or other processes, to human samples, to purified cell populations perhaps drawn from actual wild-type occurrences, and to tissue samples containing mixed cell populations. The cell or tissue sources can advantageously be plant, single celled animal, multicellular animal, bacterial, viral, fungal, yeast, or the like. The animal can advantageously be laboratory animals used in research, such as mice engineered or bred to have certain genomes or disease conditions or tendencies. The in vitro cell populations or cell lines can be exposed to various exogenous factors to determine the effect of such factors on gene expression. Further, since an unknown signal pattern is indicative of an as yet unknown gene, this invention has important use for the discovery of new genes. In medical research, by way of further example, use of the methods of this invention allow correlating gene expression with the presence and progress of a disease and thereby provide new methods of diagnosis and new avenues of therapy which seek to directly alter gene expression.

Finally, gene expression analysis can also be utilized for pharmogenomic analysis of drug action and efficacy. For example, the present invention may be used to quantitatively ascertain the mechanism of a specific drug's biological activity and why the drug(s) may fail to work as predicted. This application has utility, for example, in stratifying patient populations.

DESCRIPTION OF THE FIGURES

The present invention may be better understood and its advantages appreciated by those individuals skilled in the relevant arts by referring to the accompanying drawings wherein:

FIG. 4 provides the nucleotide sequence (SEQ ID NO: 1) of a 2493 bp. cDNA generated from the mRNA encoded by the Human Complement Component 1, Subcomponent r (C1r) gene. The bold sequence illustrates the 319 bp. subsequence generated by digestion of the C1r cDNA with the REs BspH1 and EcoR1. This cDNA was utilized with the oligo-poisoning conformation methodology of the present invention.

Panel A: Electropherogram of GeneCalling™ up trace.

Panel B: Electropherogram of the GeneCalling™ down trace.

Figure 6A:
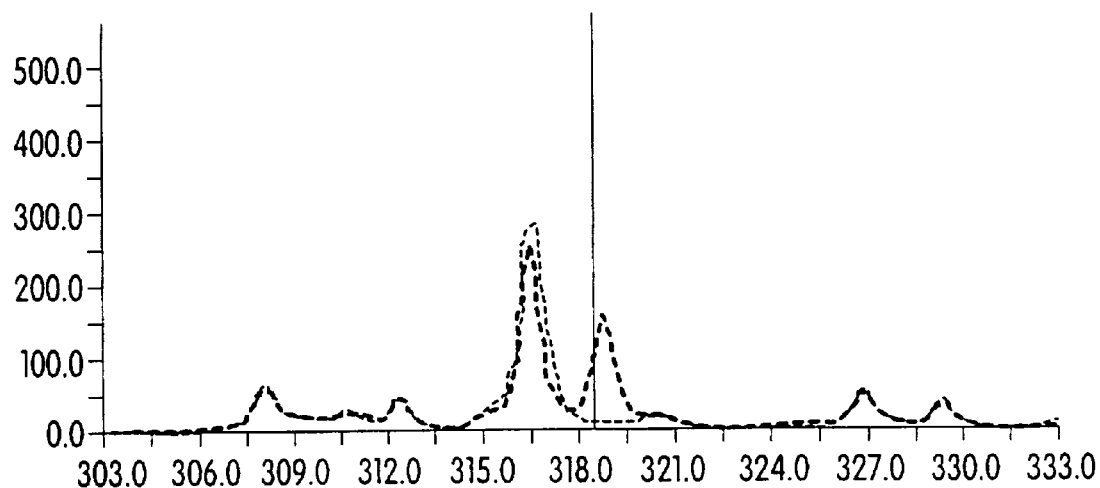
Figure 6B:
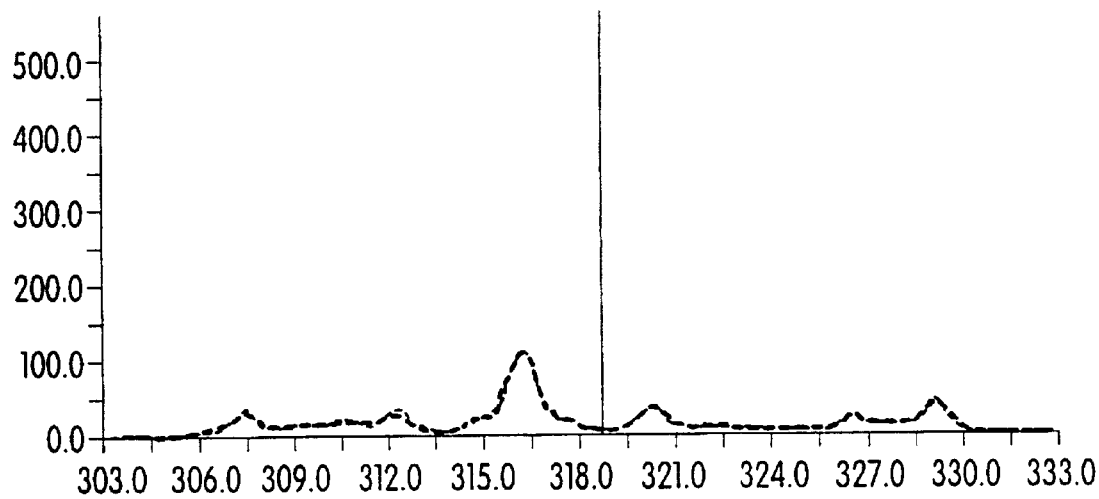

FIG. 6, Panels A & B are electropherograms of the up and down traces generated by PCR amplification of the GeneCalling™ reactions with C1r cDNA utilizing "poisoning" oligomer primers.

Panel A: Electropherogram of the oligo-poisoned GeneCalling™ up trace.

Panel B: Electropherogram of the oligo-poisoned GeneCalling™ down trace.

DETAILED DESCRIPTION OF THE INVENTION

In order that the present invention disclosed herein is better understood and appreciated, the following detailed description is set forth.

Without limitation, the oligo-poisoning methodology disclosed herein has been primarily applied in quantitative expression analysis (GeneCalling™), as disclosed in WO97115690 entitled "METHOD AND APPARATUS FOR IDENTIFYING, QUANTIFYING, AND CONFIRMING DNA SEQUENCES IN A SAMPLE WITHOUT SEQUENCING," and which is incorporated herein by reference in its entirety. However, individuals possessing ordinary skill within the relevant arts will immediately appreciate how to adapt this methodology to the other protocols for generating appropriate nucleic acids samples of the described structure. Prior to proceeding with the detailed description of the oligo-poisoning methodology, a review of GeneCalling™ methodology will be set forth.

1. Quantitative Expression Analysis (GeneCalling™)

In order to uniquely identify or classify an expressed, full or partial nucleotide or gene sequence, as well as many components of genomic DNA (gDNA), it is not necessary to determine the actual, complete nucleotide sequences, as these complete nucleotide sequences provide far more information than is needed to merely classify or determine a given nucleotide sequence according to the present invention disclosed herein. Moreover, the actual number of expressed human genes represents an extremely small fraction (i.e., $10^{-1195}$) of the total number of possible DNA sequences. Hence, the utilization of GeneCalling™ and the oligo-poisoning methodologies of the present invention, allows direct determination of nucleotide sequences (without the requirement of establishing a complete nucleotide sequence) within a heterogeneous sample by making use of a nucleic acid sequence database containing those of sequences which are likely to be present within the sample. Moreover, even if such a database is not available, sequences within the sample can, nonetheless, be individually classified.

Quantitative expression analysis (GeneCalling™) provides a methodology for identifying, classifying, or quantifying one or more nucleic acids sequences within a sample comprising a plurality of nucleic acids species each possessing different nucleotide sequences. In brief, the various steps in the preferred embodiment of GeneCalling™ methodology (i.e., the restriction endonuclease digestion/ligation/amplification-based protocol) may be summarized as follows:

Step 1: complementary DNA (cDNA) synthesis

Step 2: The resulting cDNA fragments are digested utilizing two different restriction endonucleases (RE) which, preferably, recognize only rare, 6–8 bp. RE-recognition sequences.

Step 3: Ligation of oligonucleotide "adapters" to the digested cDNA fragments. Two different adapters are utilized, with each adapter being complementary to the sequences of one of the two RE recognition sites.

Step 4: PCR amplification is performed utilizing labeled primers which are complementary to the two adapters ligated to the digested cDNA fragments.

Step 5: The reaction products of the PCR amplification are then electrophoresed to observe the electrophoretic mobility patterns of the individual fragments. These mobility patterns are then utilized to construct an electropherogram.

Step 6: From the electrophoretic mobility and electropherogram the sizes of the individual fragments of interest are identified, and a computer DNA sequence database is then searched to generate a list of putative gene "identities" for these aforementioned fragments.

Thus, the GeneCalling™ methodology is performed by hybridizing the sample with one or more labeled probes, wherein each probe recognizes a different "target" nucleotide subsequence or a different set of "target" nucleotide subsequences. The target subsequences utilized in the GeneCalling™ methodology are, preferably, optimally chosen by the computer implemented methods of this invention in view of DNA sequence databases containing sequences likely to occur in the sample to be analyzed. In respect to the analysis of human genomic cDNAs, efforts of the Human Genome Project in the United States, efforts abroad, and efforts of private companies in the sequencing of the human genome sequences, both expressed and genetic, are being collected in several available databases.

The resulting hybridization signal(s) is, preferably, comprised of a representation of (i) the presence of a first target subsequence; (ii) the presence of a second target subsequence and (iii) the length between the target subsequences in the sample nucleic acid sequence. If the first strand of target subsequences occur more than once in a single nucleic acid in the sample, more than one signal is generated, each signal comprising the length between adjacent occurrences of the target subsequences. While the target subsequences recognized are typically contiguous, the GeneCalling™ methodology is adaptable to recognizing discontiguous target subsequences or discontiguous effective target subsequences. For example, oligonucleotides recognizing discontinuous target subsequences can be constructed by inserting degenerate nucleotides within a discontinuous region. In addition, phasing primers (which possess additional nucleotide sequence beyond the RE site) may also be utilized to augment sequence specificity.

Following hybridization and target signal detection, a search of a nucleotide sequence database, comprised of known sequences of nucleic acids which may be present within the sample, is performed in order to ascertain either sequences which match or, alternately, the absence of any sequences which match the generated hybridization signal (s). A sequence contained within the database is considered to "match" (i.e., is homologous) to a generated hybridization signal when the nucleotide sequence from the database possesses both (i) the same length between occurrences of the target subsequences as is represented by the generated hybridization signal and (ii) the same target subsequences as is represented by the generated signal or, alternately, target subsequences which are members of the same sets of target subsequences represented by the generated signal.

The GeneCalling™ methodology may be applied to the analysis of complementary DNA (cDNA) samples synthesized from any in vivo or in vitro sources of RNA. cDNA can be synthesized from total cellular RNA, poly(A)' messenger RNA (mRNA), or from specific sub-pools of RNA. Such RNA sub-pools can be produced by RNA pre-purification. For example, the separation of endoplasmic reticulum mRNA species from those mRNAs contained within the cytoplasmic fraction, facilitates the enrichment of mRNA species which encode cell surface or extracellular proteins. See e.g., Celis, L., et al., 1994. *Cell Biology* (Academic Press, New York, N.Y.).

While the GeneCalling™ methodology is preferred for classifying and determining sequences contained within a sample comprised of a mixture of cDNAs, but it is also adaptable those samples which contain a single cDNA moiety. Typically, enough pairs of target subsequences can be chosen so that sufficient distinguishable signals may be generated so as to allow the determination of one, to all of the sequences contained within the sample mixture. For example, in a first possible scenario, any pair of target subsequences may occur more than once in a single DNA molecule to be analyzed, thereby generating several signals with differing lengths from one DNA molecule. In a second scenario, even if a pair of target subsequences occurred only once within two different DNA molecules to be analyzed, the lengths between the probe hybridizations may differ, and thus distinguishable hybridization signals may be generated.

In the preferred PCR-mediated GeneCalling™ methodology, a suitable collection of target subsequences is chosen via computer-implemented methods and PCR primers, preferably labeled with fluorescent moieties, are synthesized to hybridize with these aforementioned target subsequences. Advances in fluorescent labeling techniques, in optics, and in optical sensing currently permit multiply-labeled DNA fragments to be differentiated, even if they spatially-overlap (i.e., occupy the same "spot" on a hybridization membrane or a band within a gel). See Ju, T., et al., 1995. *Proc. Natl. Acad Sci. USA* 92:4347–4351. Accordingly, the results of several GeneCalling™ reactions may be multiplexed within the same gel lane or filter spot. The primers are designed to reliably recognize short subsequences while achieving a high specificity in the PCR amplification step. Utilizing these primers, a minimum number of PCR amplification steps amplifies those fragments between the primed subsequences existing in DNA sequences in the sample, thereby recognizing the target subsequences. The labeled, amplified fragments are then separated by gel electrophoresis and detected.

GeneCalling™ may be performed in either a "query mode" or in a "tissue mode." In query mode, the focus is upon the determination of the expression of a limited number of genes of interest and of known sequence (e.g., those genes which encode oncogenes, cytokines, and the like). A minimal number of target subsequences are chosen to generate signals, with the goal that each of the limited number of genes is discriminated from all the other genes likely to occur in the sample by at least one unique signal. Conversely, in tissue mode, the focus is upon the determination of the expression of as many as possible of the genes expressed in a tissue or other sample, without the need for any prior knowledge of their expression. In the tissue mode, target subsequences are optimally chosen to discriminate the maximum number of sample DNA sequences into classes comprising one, or preferably at-most a few sequences. Ideally, sufficient hybridization signals are generated and detected so that computer-based identification methods can uniquely determine the expression of a majority, or more preferably most, of the genes expressed within a given tissue. It should be noted, however, that in both modes, hybridization signals are generated and detected as determined by the threshold and sensitivity of a particular experiment. Important determinants of threshold and sensitivity include, but are not limited to: (i) the initial amount of mRNA and thus of cDNA utilized; (ii) the amount of PCR-mediated amplification performed and (iii) the overall sensitivity and discrimination capability of the detection means utilized.

a) The Preferred PCR-Mediated GeneCalling™ Methodology

The preferred embodiment of the GeneCalling™ methodology is based upon the utilization of polymerase chain reaction (PCR) amplification, or alternative amplification means, to select and amplify cDNA fragments between the target subsequences of interest recognized by the chosen, labeled PCR amplification primers. The methodologies utilized in PCR amplification reactions are well-known to those individuals skilled within the relevant fields. See generally, Innis, et al., 1989. *PCR Protocols: A Guide to Methods and Applications*, (Academic Press; New York, N.Y.); Innis, et al., 1995. *PCR Strategies*, (Academic Press; New York, N.Y.).

In the typical GeneCalling™ PCR amplification reaction, target subsequences between 4 and 38 base pairs (bp) in length are preferred because of their greater probability of occurrence, and hence information content, as compared to longer subsequences. However, oligonucleotide sequences of this length may not hybridize reliably and reproducibly to their complementary subsequences to be effectively used as PCR primers. Hybridization reliability depends strongly on several variables, including, but not limited to: primer composition and length, stringency condition such as annealing temperature and salt concentration, and cDNA mixture complexity. In the PCR-mediated GeneCalling™ methodology, it is highly preferred that target subsequence recognition be as specific and reproducible as possible so that well resolved bands representative only of the underlying sample sequence are produced. Thus, instead of directly using single short oligonucleotides complementary to the selected, target subsequences as primers, it is preferable to use carefully designed primers.

Figure 1:
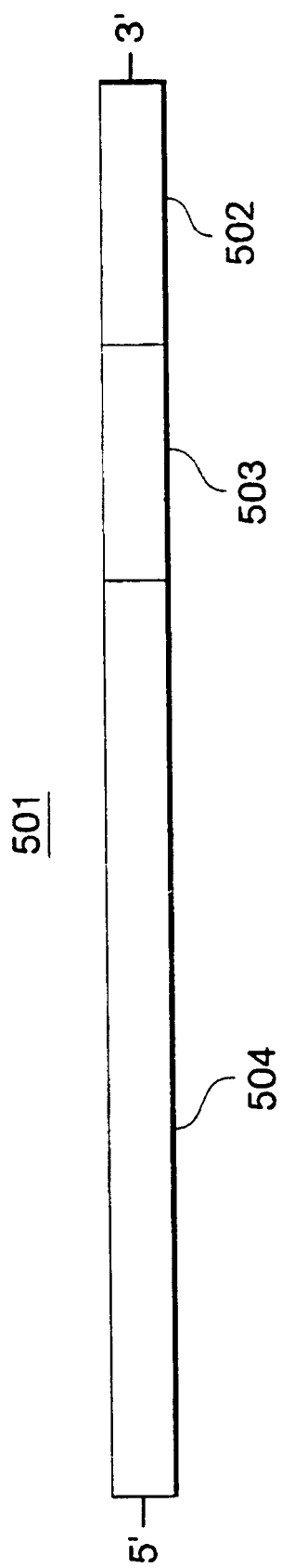
FIG. 1 is an illustration of the DNA primers utilized for a PCR amplification-mediated embodiment of the GeneCalling™ methodology.

The preferred PCR amplification primers are constructed according to the model illustrated in FIG. 1. As per this figure, Primer 501 is constructed of three individual component sequences (listed in the 5' to 3' orientation) which include: Components 504, 503, and 502. It should be noted that Although Component 503 is optional, it can be utilized to improve the specificity of the first low stringency annealing step during PCR amplification, and thereby mitigate the production of false positive amplification products. Component 502 is a sequence which is complementary to the subsequence which primer 501 is designed to recognize. Component 502 is typically 4–8 bp in length. Component 504 is a 10–20 bp sequence chosen so the final primer does not hybridize with any native sequence in the cDNA sample to be analyzed; that is, primer 501 does not anneal with any sequence known to be present in the sample to be analyzed. The sequence of component 504 is also chosen so that the final primer has a melting temperature (T.) above 50° C. and preferably, above 68° C.

Use of primer 501 in the PCR amplification involves a first annealing step, which allows the 3' terminal Component 502 to anneal to its target subsequence in the presence of Component 504, which may not hybridize. Preferably, this annealing step is performed at a temperature (generally between 36° C. and 44° C.) which is empirically determined so as to maximize the reproducibility of the resulting hybridization signal pattern. The DNA concentration is approximately 10 ng/50 ml and is similarly determined to maximize reproducibility. Once annealed, the 3'-terminus serves as the primer elongation point for the subsequent first elongation step. The first elongation step is preferably performed at 72° C. for 1 minute. If stringency conditions are such that exact complementarity is not required for primer annealing, false positive signals (i.e., signals resulting from inexact recognition of the target subsequence) may be generated. Subsequent cycles utilize high temperature, high stringency annealing steps. The high stringency annealing steps ensure annealing of the entire primer to the fragment sequences of interest. Preferably, these PCR cycles alternate between a 65° C. annealing step and 95° C. melting step, with each step lasting for 1 minute.

As previously discussed, optional Component 503 may be utilized to improve the specificity of the first low stringency annealing step, and thereby minimize the production of false positive bands. Component 503 may possess the generic formula —$(N)^j$—; where N is any nucleotide and j is typically between 2 and 4, preferably 2. Use of all possible Component 503 configurations results in a degenerate set of primers which have a 3'-terminus subsequence which is effectively "j" nucleotides longer in length than that of the target subsequence. These extended complementary end sequences have improved hybridization specificity. Alternately, Component 503 can be where N is a "universal" nucleotide and j is typically between 2 and 4, preferably 3 or 4. A universal nucleotide (e.g., inosine), is one which capable of forming base pairs with any other naturally occurring nucleotide. In this alternative, single primer 501 has a 3'-terminal subsequence effectively j bases longer than the target, and thus also has improved hybridization specificity.

A less preferred primer design comprises sets of degenerate oligonucleotides of sufficient length to achieve specific and reproducible hybridization, where each member of a set includes a shared subsequence complementary to one selected, target sequence. These sets of degenerate primers permit the recognition of discontinuous subsequences. Each primer or primer set utilized in a single reaction is preferably distinctively labeled for detection. In the preferred embodiment using electrophoretic fragment separation, labeling is by fluorochromes that can be simultaneously distinguished with optical detection means.

An exemplar experiment is briefly summarized below. Total cellular mRNA or purified sub-pools of cellular mRNA are utilized for cDNA synthesis. First strand cDNA synthesis is performed using, for example, an oligo(dT) primer or phasing primers. Alternatively, cDNA samples can be prepared from any source or be directly obtained. Next, using a first strand cDNA sample, the primers of the selected primer sets are used in a conventional PCR amplification protocol. A high molar excess of primers is preferably used to ensure only fragments between primer sites which are adjacent on a target cDNA subsequence or gene are amplified. With the high molar excess of primers ostensibly binding to all available primer binding sites, no amplified fragment should include any primer recognition site within its "internal" sequence. It should be noted that as many primers can be utilized in one reaction as can be labeled for concurrent separation and detection, and which generate an adequately resolved length distribution. Following amplification, the fragments are separated, re-suspended for gel electrophoresis, electrophoretically-separated, and optically detected.

This following section discloses the preferred PCR amplification protocols for the PCR embodiment of GeneCalling™. As previously discussed, this embodiment is based upon PCR amplification of fragments between target subsequences recognized by PCR primers or sets of PCR primers. It is designed for the preferred primers described with reference to FIG. 1. It should be noted that if other primers are used (e.g., sets of degenerate oligonucleotides) the first low stringency PCR cycle is omitted. PCR amplification with defined sets of primers is performed according to the following protocol:

Step 1: RNase treat the 1st strand mix with 1 μl of RNase. Cocktail from Ambion, Inc. (Austin, Tex.) at 37W for 30 minutes.

Step 2: Phenol/CHCl₃ extract the mixture 2 times, and purify it on a Centricon 100 (Millipore Corporation; Bedford, Mass.) using water as the filtrate.

Step 3: Bring the end volume of the cDNA to 50 4 (starting with 10 ng RNA/μl).

Step 4: Set up the following PCR Reaction:

| Component | Volume |
| --- | --- |
| cDNA (~10 ng/μL) | 1 μl |
| 1OX PCR Buffer | 2.5 μl |
| 25 mM MgCl₂ | 1.5 μl |
| 10 mM dNTPs | 0.5 μl |

-continued

| Component | Volume |
| --- | --- |
| 20 pM/μl primer 1 | 2.5 μl |
| 20 pM/μl primer 2 | 2.5 μl |
| Taq Poly. (5 U/μl ) | 0.2 μl |
| Water | 14.3 μl |

Step 5: One low stringency cycle with the Profile:
 40° C. for 3 minutes (annealing)
 72W for 1 minute (extension)
Step 6: Cycle using the following profile:
 95° C. for 1 minute (15–30 times):
 95° C. for 30 seconds
 50° C. for 1 minute
 72° C. for 1 minute
 72° C. for 5 minutes
Step 7: 4° C. hold.
Step 8: Samples are precipitated, resuspended in denaturing loading buffer, and analyzed by electrophoresis (either under denaturing or non-denaturing conditions).

2. Oligo-Poisoning Methodology

Without limitation, the following description of the oligo-poisoning methodology has been primarily directed towards application to GeneCalling.™ However, an individual of ordinary skill within the relevant arts will immediately appreciate how to adapt this description to other protocols for generating appropriate nucleic acids samples of the described structure.

Oligo-poisoning is applicable for nucleic acid fragments of any size which possess the ability to undergo PCR amplification, including, but not limited to, those nucleic acid fragments typically present within GeneCalling™ reaction products which generally range in size from 30–600 bp. in length. Typically, the oligo-poisoning methodology proceeds by performing a PCR amplification of GeneCalling™ reaction products utilizing an amplification which is designed to produce detectable results for those amplification products which do not possess a putatively identified sequence. In the preferred embodiment, this result is achieved by adding a molar excess of an unlabeled "poisoning" primer which is designed to amplify only those fragments having the putatively identified sequence. Accordingly, all amplification products of such fragments are unlabeled and not detectable. However, it should be noted that oligo-poisoning is also equally applicable to confirming putative sequence identifications in any sample of nucleic acid fragments which possess a defined "generic" structure or motif which will be discussed supra. The only imposed limitation is that these nucleic acid fragments must possess known terminal subsequences which are capable of acting as PCR primers. Several methodologies for producing nucleic acids with such a generic structural motif are well-known to those individuals skilled in the art.

The aforementioned generic structural motif is comprised of nucleic acid species possessing known terminal subsequences on both their 3'- and 5'-termini which flank a central subsequence of interest. While the central subsequence may be of any length, a minimum length of approximately IO bp. is preferred in the present invention. The terminal subsequences, which may be different, are of such length and base composition as to permit reliable and specific primer annealing for subsequent PCR amplification under stringent conditions. In order to obtain the required degree of specificity, the lengths of the known terminal subsequences are, preferably, at least 10 bp., and can be up to greater than 20–30 bp. in length. The central subsequence determines the "identity" of the specific nucleic acid species, and is thereby to be compared with the putatively identified sequence. Hence, confirmation is obtained if a fragment exists within the sample which possess a central subsequence having a sequence which is (at a minimum) homologous to a portion of the putatively identified sequence.

Nucleic acids possessing this generic structural motif are, preferably, produced according to the GeneCalling™ methods of this invention. As will be described in Section 2(a) supra, a preferred embodiment of the oligo-poisoning methodology is utilized in confirming that a specific sequence, obtained through the use of a nucleic acid sequence computer database, which has been predicted to generate a particular GeneCalling™ signal is, in actuality, generating the signal. Nonetheless, this embodiment of the oligo-poisoning methodology is not limited to confirming the results of the GeneCalling™ methodology, and can be equally applied to the confirming the results obtained from any other protocol utilizing nucleic acid species possessing the previously described generic structural motif. Therefore, as will be apparent to those of skill in the art, the oligo-poisoning confirmation methodology may be, more generally, utilized to confirm a putative sequence identification of a fragment within a sample of nucleic acid fragments possessing the aforementioned generic structural motif, that is, possessing known terminal subsequences of a length adequate to permit reliable and specific primer hybridization under stringent conditions for PCR amplification.

While several methods have been described in the art for the generation of such nucleic acid species from biological nucleic acid samples, it should be noted, however, that the Applicants do not hereby admit that any of the subsequently described examples contained herein are prior art to their invention. Three such exemplar methodologies will now be briefly described. A first method is disclosed in European Patent Application 0 534 858 A1, entitled "Selective Restriction Fragment Amplification: A General Method for DNA Fingerprinting," and which is incorporated by reference herein in its entirety. According to this method, a sample of cDNA is initially digested with restriction endonucleases ("RE") into fragments and oligonucleotides complementary to these digested fragments are hybridized to the fragments. A longer primer strand of each adaptor is then ligated to the fragments. These products are then PCR amplified using PCR primers which include the longer primer strands. For selective amplification, these primers can, optionally, extend for 1–10 selected nucleotides beyond any remaining portion of the RE recognition site. Since fragments in the unamplified, amplified, and selectively amplified samples are all terminated by known primer sequences, this method generates nucleic acid samples of the described generic structure. In accord with this method, the sequences of individual fragments within these samples can be putatively identified by partial or complete sequencing.

A second method is described in U.S. Pat. No. 5,459,037, entitled "Method for Simultaneous Identification of Differentially Expressed mRNAs and Measurement of Relative Concentrations," which is incorporated by reference herein in its entirety. As disclosed by this method, cDNAs are synthesized using a first-strand oligo(dT) primer which includes two phasing nucleotides and a recognition site for a rare-cutting RE. The resulting cDNAs are then digested by both the rare-cutting RE and a more frequently-cutting RE. The digested fragments are ligated in an anti-sense orientation into a cloning vector, which is subsequently used to synthesize complementary RNA (cRNA). Next, cDNA is synthesized from this cRNA using first-strand primers having sequences corresponding to the portion of the cloning vector adjacent to the 3'-termini of each insert, as well as including two phasing nucleotides. Finally, the resulting products are PCR amplified using primers comprising adjacent portions of the cloning vectors on both sides of the insert, with one of these primers having optional phasing nucleotides. Since nucleic acid fragments in all the multiple, possible pools of final samples are terminated by known primer sequences, this methodology generates nucleic acid species of the previously-described generic structural motif. According to this method, the sequences of individual fragments in these samples can be putatively identified by partial or complete sequencing.

A third method is described in Prashar, et al., 1996. Analysis of Differential Gene Expression by Display of 3'-End Restriction Fragments of cDNAs, *Proc. Nat. Acad. Sci. USA* 93:659–663, which is incorporated by reference herein in its entirety. As disclosed by this method, cDNA is synthesized using an oligo(dT) first-strand primer possessing two phasing nucleotides at the 3'-terminus and a special "heel" subsequence at the 5'-terminus. After digestion with a frequently-cutting RE, a partially double-stranded "Y"-adapter is annealed and ligated onto the RE-digested termini of the cDNA fragments. This "Y"-adaptor possess a non-complementary region including a 5'-primer sequence. Finally, PCR amplification of the ligated fragments, which are primed with a first primer having the heel primer sequence and a second primer having the 5'-end primer sequence, produces a pool of fragments which have been terminated by these aforementioned sequences. Similarly, since the pool of final fragments are terminated by known primer sequences, this method generates nucleic acid species of the previously-described generic structural motif. According to this method, the sequences of individual fragments in these samples can be putatively identified by partial or complete sequencing.

As previously discussed, oligo-poisoning confirmation is also adaptable to other methodologies which utilize nucleic acid fragment samples having the aforementioned generic structural motif which are either known within the art, or subsequently described in the future. As confirmatory oligo-poisoning methodologies are, preferably, applied to GeneCalling™ reaction products, they are described in the following subsection primarily with respect to such GeneCalling™ reaction products. However, this description is without limitation, as individuals possessing ordinary skill within the relevant arts will readily appreciate how to adapt oligo-poisoning methodologies to any sample of nucleic acids which possess the previously-described generic structural motif, including nucleic acid species produced by the aforementioned methods and the like.

(a) Conformation of a Putative Sequence by the Oligo-Poisoning Methodology

The oligo-poisoning methodology disclosed herein may be utilized to confirm a putative sequence which has been identified for a nucleic acid fragment, within a sample of nucleic acids, possessing the previously-described generic structural motif. The oligo-poisoning methodology depends upon the knowledge of, and serves to confirm the nucleotide sequence of, a portion of a unique, central nucleic acid sequence of interest, which is spatially located adjacent to known terminal subsequences. It has been ascertained that the knowledge of (at a minimum) the sequence of a portion of a fragment is, in fact, sufficient to confirm that a putative, candidate sequence, or which one of a small number of putative, candidate sequences, is actually the sequence of the nucleic acid species of interest.

For example, in the case of GeneCalling,™ fragments are, preferably, putatively identified by the computer-based GeneCalling™ analysis methods applied to the resultant GeneCalling™ signals. Even within complex genomes, it has been determined that the computer-based methods typically determine 1 or 2, usually less than 5, and almost invariably less than 10, potential "candidate" sequences for a particular GeneCalling™ signal. Accordingly, knowledge of only a few additional nucleotides of sequence is sufficient to verify which of the putative "candidate" sequences is actually the fragment producing the GeneCalling™ signal. Furthermore, such knowledge is also sufficient to differentiate known candidate sequences from previously uncharacterized nucleic acids.

Moreover, it has been demonstrated that information derived from a GeneCalling™ signal, in combination with information representing an additional 4 bp. (at a minimum) or, preferably, 8 bp. or, more preferably, 12 or more base pairs, is almost always sufficient to uniquely determine the sequence generating a GeneCalling™ signal of interest. Accordingly, in the preferred GeneCalling™ application, the oligo-poisoning methodology functions to confirm that a particular fragment generates a particular signal of interest by "checking" the nucleic acid sequence identity of an additional subsequence of the aforementioned length, which are present in both the fragment and in the putatively identified sequence as determined from the nucleic acid sequence database.

Generally, the oligo-poisoning methodology proceeds by the amplification of nucleic acid fragments within a nucleic acid sample of the described generic structural motif under reactions conditions such that the particular fragment of interest is amplified in a distinctively different manner only if it possesses the putatively identified nucleotide sequence. More specifically, oligo-poisoning includes performing PCR amplification of nucleic acid samples utilizing rationally-designed "poisoning" primers, concomitantly with the typical PCR amplification primers which are capable of annealing to known, terminal subsequences for the purposes of facilitating PCR amplification (such primers hereinafter will be referred to as "regular primers"). In contrast, the "poisoning" primers are constructed so as to either suppress or distinctively (i.e., differentially) label signals from the PCR-amplified nucleic acid fragment possessing the putatively identified sequence of interest. Suppression of the signal may be performed by either competitive hybridization with the fragment of interest or by preventing its elongation once hybridized. For example, with respect to GeneCalling,™ the oligo-poisoning methodology requires performing PCR amplification of the GeneCalling™ reaction products using the rationally-constructed "poisoning" primer, in addition to the "regular" PCR amplification primers which possess the sequence of the GeneCalling™ adapter primer strands.

The confirmation of the GeneCalling™ sequence identification for a nucleic acid of interest utilizing the oligo-poisoning methodology is, preferably, performed in the following manner. An aliquot of the nucleic acid sample is PCR amplified with the previously described regular primers along with a 100 to 1000-fold molar excess of the "poisoning" primers, thus producing "poisoned" PCR amplification reaction products. If the nucleic acid sample had been previously PCR amplified, as in GeneCalling™ methods, this aliquot is diluted prior to performing the subsequent amplification utilizing the "poisoning" primers. The amplified aliquot is then separated, preferably, via gel electrophoresis, and the resultant separated bands are detected and analyzed in an appropriate manner (i.e., automated optical detection with the generation of an electropherogram). The results of the oligo-poisoning amplification reaction may then be compared with those results obtained from the original GeneCalling™ amplification reaction. This comparison allows any differences in the electrophoretic banding patterns and/or electrophoretic mobility of the nucleic acid fragments, especially any such differences in the band representing the fragment of interest, to be noted.

Accordingly, if the nucleic acid fragment of interest possesses a correctly identified putative sequence, only that band containing that nucleic acid fragment will either be absent or display altered electrophoretic mobility. The bands representing the other fragments will again be present to the same extent as found for the original amplification, electrophoretic separation, and detection performed without the "poisoning" primers. In contrast, if the fragment of interest possesses an incorrectly identified putative sequence, the band containing that fragment will, upon electrophoretic separation and detection, again be present to the same extent as found for the original amplification, electrophoretic separation, and detection performed without the "poisoning" primers. Therefore, in the incorrect identification scenario, the addition of the "poisoning" primers will have no demonstrable affect on the nucleic acid banding pattern obtained by electrophoretic separation of the PCR amplification reaction products.

In brief, the PCR amplification-mediated, oligo-poisoning methodology, as applied to GeneCalling™ confirmation, is comprised of the following steps:

Step 1: A PCR amplified GeneCalling™ reaction is performed.

Step 2: Utilizing the electrophoretic mobility results obtained from the electrophoresis of the GeneCalling™ PCR amplification reaction products in combination with those putative sequence "identity" results obtained from the utilization of the nucleic acid sequence database, a set of two "poisoning" oligonucleotide primers are designed, wherein each of the "poisoning" primers is complementary to one of the two RE initially utilized to digest the cDNA fragments (see Section 1; Step 2). The design of the "poisoning" primers incorporates: (i) sequence which is homologous to the RE-specific adapter sequence (See Section 1; Step 3) on their 5'-termini and (ii) sequence which is homologous to 10–20 bp. of the unique, central subsequence of interest on their 3'-termini.

Step 3: A second PCR amplification is performed on the original GeneCalling™ reaction. PCR amplification reaction products with the addition of a 100 to 1000-fold molar excess of, preferably, unlabeled "poisoning" primers possessing the nucleotide sequence as described in Step 2 and "regular" PCR primers. High stringency primer annealing conditions are utilized to ensure adequate specificity.

Step 4: The reaction products of the oligo-poisoned PCR amplification are then electrophoresed to observe the electrophoretic mobility patterns of the individual fragments and an electropherogram is constructed. These results are then compared with those obtained from the original, original GeneCalling™ PCR amplification reaction performed without the addition of the "poisoning" primers.

Step 5: Steps 2–4 are repeated until "poisoning" primers are identified which have an affect on the electrophoretic band(s) containing the sequence of interest. Thus, if the "poisoning" primer is correctly designed (i.e., possesses sequence which is complementary to the sequence of interest), the electrophoretic banding patterns of the PCR amplification reactions with and without "poisoning" primer will be altered. Specifically, the band(s) containing the putatively identified sequence will either be absent or have altered electrophoretic mobility in the "poisoning" primer-containing PCR amplification reaction.

Figure 2:
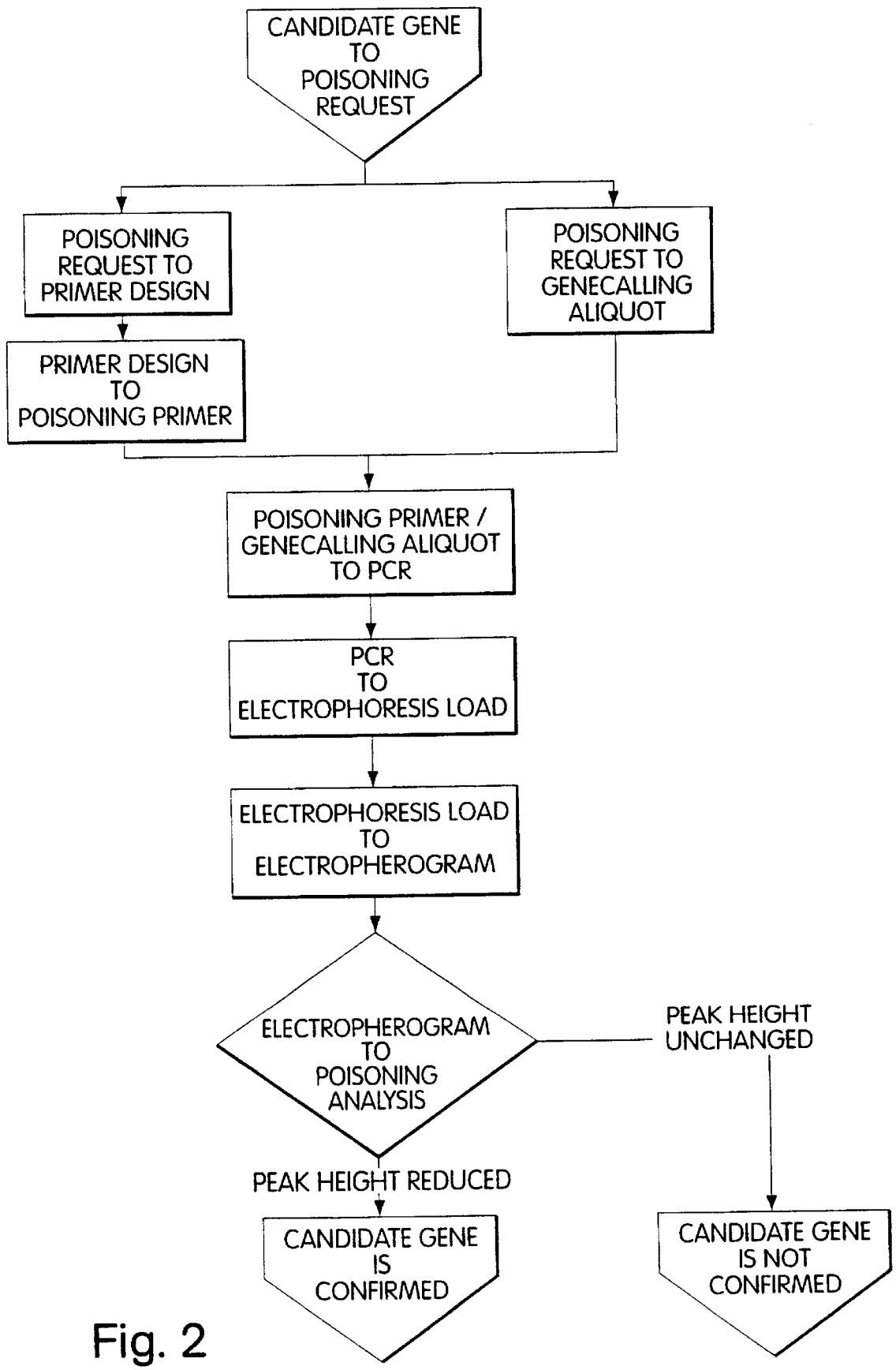
FIG. 2 is a flow chart illustrating the various steps utilized in the oligo-poisoning methodology of the present invention as applied to the conformation of the results obtained from GeneCalling.™

In addition, these aforementioned steps are illustrated in a flow chart in FIG. 2.

The oligo-poisoning methodology can also advantageously be applied to nucleic acid fragments of interest in each of two or more samples of nucleic acids which possess the previously-described generic structural motif. Such samples may be obtained, for example, from two or more comparable tissue samples which are in different biological "states." In the aforementioned case, oligo-poisoning may be utilized to confirm the putative identification of fragments having expression differences between the samples (i.e., exhibiting differential expression), and to determine whether a novel nucleic acid is generating such expression differences.

For example, in the case of a fragment of interest which has been determined to be differentially expressed in each of two tissue samples (e.g., by a previous electrophoretic comparison) and which has been identified as possibly possessing two or more putative candidate sequences, the sequential "poisoning" of the fragments with two "poisoning" primers (each constructed to "poison" one of the two candidate sequences) may be utilized to identify the differential and relative presence of each candidate sequence within each tissue. In one potential scenario, the expression of both candidate sequences may be differentially increased within the same tissue sample, thus leading to a greater differential expression of the fragment of interest between the two tissues. In a second potential scenario, the expression of the candidate sequences may be differentially increased within different tissue samples, leading to a lesser differential of the fragment of interest. The oligo-poisoning methodology possesses the ability to ascertain which of these potential scenarios is correct.

(b) Preferred PCR Amplification Methodology Utilizing Oligo-Poisoning

Figure 3A:
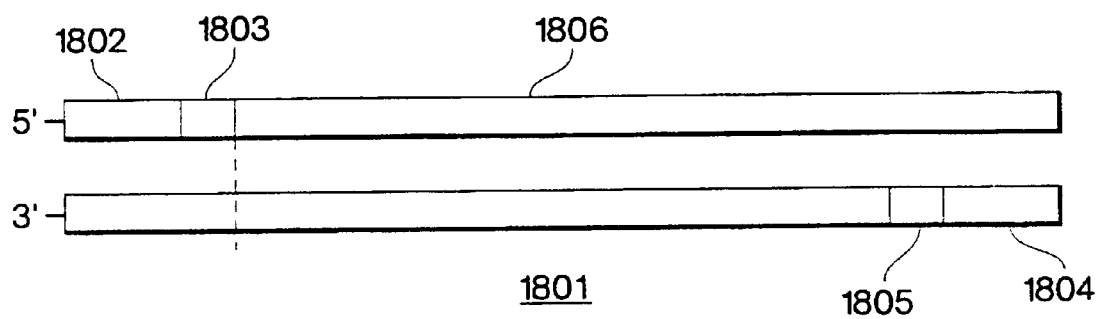
FIG. 3, Panels A & B are schematic diagrams illustrating the preferred construction of the "poisoning" primers utilized in the oligo-poisoning methodology of the present invention as applied to the conformation of the results obtained from GeneCalling.™

The oligo-poisoning methodology is outlined below in detail first, with respect to construction of "poisoning" primers and second, with respect to the PCR amplification reaction conditions utilizing the "poisoning" primers. The following guidelines, described with respect to FIGS. 3A and 3B, set forth the preferred criteria for the generation of "poisoning" primers. These figures illustrate the preferred application of oligo-poisoning to GeneCalling™ reactions and any differences which are appropriate for general application will be described as necessary. FIG. 3A illustrates an exemplar dsDNA fragment ("fragment 1801")which is present in GeneCalling™ reaction products following adapter ligation and PCR amplification. Each strand of double-stranded fragment 1801 possesses: (i) a known 5'-terminal (and, therefore, a known complementary 3'-terminal) subsequences and (ii) a putatively identified central subsequence ("subsequence 1806") which is to be confirmed by utilization of the oligo-poisoning methodology.

The known 5'-terminal subsequence consists (on the upper DNA strand) of concatenated subsequences 1802 and 1803, and (on the lower DNA strand) of concatenated subsequences 1804 and 1805. Subsequences 1802 and 1804 have the same sequence as that of the adapter primers which were ligated onto the termini of the sample nucleic acid, thus generating fragment 1801 following RE digestion. With respect to the ligation of the adapter primers, two different scenarios are possible. In the first scenario (in which the termini of fragment 1801 are digested by different REs), different adapter primers are preferably ligated and subsequences 1802 and 1804 are different. In the second scenario (in which the termini of fragment 1801 were digested by the same RE), subsequences 1802 and 1804 are the same.

Adjacent to subsequences 1802 and 1804 are further subsequences 1803 and 1805, which are the portions of the RE recognition sites remaining after the original RE digestion. For example, when the RE which was utilized to digest the left-terminus of fragment 1801 has a 6 bp. recognition site and results in the generation of a 4 nt. "overhang" following digestion, subsequence 1803 will have a length of 5 nt.

The final subsequence, central subsequence 1806, possesses a candidate sequence, putatively identified either by computer-based analysis methods known within the field or by nucleic acid sequencing of the fragment. The oligo-poisoning methodology is to be utilized to confirm that nucleic acid fragments possessing the putatively identified sequence are: (i) actually present within the sample and (ii) actually generating the GeneCalling™ signal of interest.

In the general case of nucleic acid species possessing the previously-described generic structural motif, subsequences 1802 and 1804 represent the known terminal subsequences; whereas subsequences 1803 and 1805 may be absent depending upon the generation method used. It is then to be confirmed that a putatively identified sequence is actually present in a fragment within the sample.

Figure 3B:
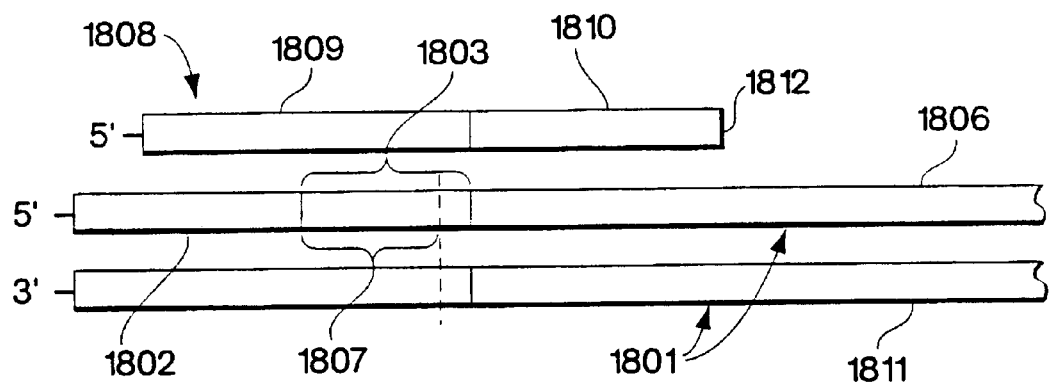

FIG. 3B, which details the left-terminus of fragment 1801 shown in FIG. 3A, illustrates "poisoning" primer 1808, which is directed towards a GeneCalling™ application. "Poisoning" primers may be constructed and used for either termini of fragment 1801. In addition, the "poisoning" primers constructed for both termini of fragment 1801 may be utilized simultaneously in a single PCR amplification. FIG. 3B also illustrates: (i) subsequence 1802 (possessing the sequence of the ligated adapter primer); (ii) subsequence 1803 (possessing the sequence of the remaining portion of the RE recognition site) and (iii) the 5'-terminus of central subsequence 1806. Subsequence 1807 is in the position of the overhang formed by RE digestion. "Poisoning" primer 1808 consists of 5'-terminus subsequence 1809 and 3'-terminus subsequence 1810.

Therefore, in more simplified terms, 5'-terminus subsequence 1809 possesses the same sequence as the known subsequence 1803 concatenated with the 3'-terminus of known subsequence 1802. Similarly, 3'-terminus subsequence 1810 possesses the same sequence as the adjacent portion of the 5'-terminal strand of central subsequence 1806, for which a partial or full candidate sequence has already been putatively identified. Hence, in view of recited structure of dsDNA fragment 1801, the "poisoning" primer is capable of annealing to the 3'-strand 1811 to facilitate PCR amplification of fragment 1801. The length of subsequence 1810 is chosen such that it reliably and specifically anneals to the complementary portion of strand 1811 under stringent hybridization conditions. The preferred, stringent hybridization conditions will be disclosed supra.

In the general case of nucleic acids species possessing the previously-described generic structural motif, subsequences 1809 is that of the 3'-terminus of the corresponding known terminal subsequence. Subsequence 1807 may be absent. Poisoning primer 1808 is preferably constructed according to the following specification in order for it to reliably and specifically recognize the putatively identified sequence for central subsequence 1806 under stringent hybridization conditions. For such stringent hybridization, subsequence 1810 is, preferably, 8–16 nt. in length, and is of sufficient length such that the 3'-terminus nucleotide 1812 of the "poisoning" primer is G or C. The most preferable length of subsequence 1810 is approximately 12 nucleotides. For reliable, specific and stringent hybridization, it is also preferable for the G+C content of subsequence 1810 to be at least approximately 40%, or more preferably from 50–60%, or greater. Therefore, a "poisoning" primer is preferably constructed and utilized for annealing to the terminus of the fragment containing the greatest overall G+C content. Additionally, the length of subsequence 1809 is such that the total length of "poisoning" primer 1808 is preferably between 18 and 30 nt. and most preferably between 19–23 nt. in order to facilitate reliable, specific, and stringent primer annealing. Where the length of remaining portion 1803 of the RE recognition site is comprised of 5 nt. and the length of 3'-terminus subsequence 1810 is 14 nt., 5'-terminus subsequence 1809, most preferably, possesses the same sequence as the 0–4 nt. long, 3'-terminus of adapter primer sequence 1802.

As previously discussed, a "poisoning" primer constructed pursuant to these aforementioned specifications is advantageously capable of specifically annealing to its complementary sequence under stringent hybridization conditions. For example, preferably, the melting temperature ($T_m$) of the "poisoning" primer is in the range from 5° C. to 80° C., and more preferably, above 68° C. Such preferred $T_m$ may be achieved, as is well-known within the art, by an appropriate G+C content or by the use of an appropriately long nucleotide sequence. For example, a preferable G+C content is from 40–60%. Therefore, where the composition of the 5'-terminus of central subsequence 1806 includes a higher percentage of A+T, subsequence 1810 should be chosen to be longer than when the A+T percentage is lower. Further, it is preferable that the "poisoning" primer be constructed so as to be free of secondary structure, as well as not being complementary to any sequences likely to occur within the sample being analyzed. In the case of application to GeneCalling,™ these condition permit the temperature profile of the PCR amplification to be controlled so that linkers (which originate from the adapters used in the RE/ligase reactions and remain in the GeneCalling™ reaction products sample) are not able to hybridize and to initiate new oligonucleotides.

It is important that signals produced from products resulting from "poisoning" primer-initiated amplifications be either not detectable or, alternatively, distinctively detectable. In a preferred embodiment, such product signals are not detectable, that is, they are "poisoned," due to the fact that "poisoning" primer 1808 is an unlabeled oligonucleotide, whereas the regular PCR primers are labeled by standard methods as known in the art (e.g., a fluorescent label). In this case, the PCR reaction results in amplification of fragment 1801, but the amplification products will not be labeled and thus not detectable. Alternatively, "poisoning" primer 1808 can be constructed such that it will disrupt amplification of fragment 1801 within the PCR reaction. For example, 3'-terminus nucleotide 1812 may be a dideoxynucleotide which is incapable of being extended by DNA polymerases and hence results in the termination of the PCR amplification. Other methods of disrupting DNA polymerase enzyme activity known in the art can also be applied.

In an additional embodiment, the "poisoning" primers are distinctively labeled such that they may be differentiated from all the other products produced by the PCR amplification reaction. For example, the "poisoning" primer can be labeled with a fluorescent dye which can be distinguished from all other dyes or labeling moieties used with other PCR primers present in the reaction. In further additional embodiment, the oligo-poisoning reaction may be multiplexed such that multiple "poisoning" primers may be utilized in a single PCR amplification reaction.

In this embodiment, the individual "poisoning" primers are differentially labeled (e.g., labeled with different fluorescent moieties), thus allowing each primer to be detected without interference from the other labeled "poisoning" primers.

PCR amplification reaction conditions (also referred to herein as "amplifying conditions") are preferably chosen in order that amplified fragments from the "poisoning" primers are reproducibly, reliably, and specifically generated. In particular, stringent annealing conditions, including high annealing temperatures, are preferable in order to minimize mis-hybridization artifacts (i.e., "noise"). A preferred annealing temperature is 57° C. or greater. Also the concentration of nucleic acids in the sample must be such that PCR amplification does not saturate and allow residual fragments from the input sample to obscure subsequent separation and detection. Alternately, the biotin clean-up procedure described can be used to eliminate residual fragments from the input sample. Where nucleic acid fragment samples have been previous amplified, as in the GeneCalling™ method, the samples are preferably diluted before PCR amplification with the "poisoning" primer in order that amplified fragments can be clearly distinguished from any residual fragments left from the input sample. Such a dilution is preferably at least 1:50 (v/v), and is more preferably 1:100 (v/v) in order to reduce residual fragment concentration to an approximately 1% or less background level, and can be 1:1000 (v/v) or greater in order to resolve especially ambiguous or low concentration fragments. In addition, in order that the amplification of all fragments with a candidate identified sequence is substantially solely due to the "poisoning" primers and not due to the adapter primers, the "poisoning" primers are preferably present in a molar excess to the regular adapter primers. This molar excess is preferably at least 1:50, and is more preferably 1:100 in order to reduce amplification of fragment having the "poisoned" sequence to an approximately 1% or less background level, and can be 1:1000 or greater in order to resolve especially ambiguous or low concentration fragments.

Generally, other parameters of the PCR reactions are preferably similar or identical to those used in the generation of GeneCalling™ signals. This is especially advantageous in the case of application of oligo-poisoning to GeneCalling™ because poisoned signals can be readily compared to the initial GeneCalling™ signals. Such PCR parameters are advantageous also in the case of oligo-poisoning applied to nucleic acid samples produced according to other methods. Oligo-poisoning also is adaptable to other high-stringency PCR protocols known in the art. Details of the preferred, exemplar PCR protocol will be disclosed in a subsequent section. In particular, it is preferred that a "hot-start" PCR method be used, and this preferred "hot-start" method also include the use of the wax layering technique described supra.

In this application of this wax technique, PCR reaction vessels are set up by placing dNTPs and water in the lower portion of a reaction vessel; layering wax on top of this dNTP solution; and placing the remainder of the PCR reaction mix on top on the wax layer. As previously described, the wax used preferably melts rapidly at near but less than 72° C., the temperature preferred for the extension phase of the PCR amplification. During PCR amplification, the first thermal cycle begins with a denaturing temperature of approximately 96° C., which is adequate to melt the wax, cause mixing of the reagent compartments, and initiate amplification. The PCR thermal profile is performed, as described in the following section with a preferred stringent annealing temperature of at least approximately 57° C. Also, one primer of the pair of regular primers used in the PCR amplification can be biotin labeled. In this case, the PCR reaction products are then processed according td one of the biotin-bead cleanup procedures, known in the art, in order to remove fragments from the input sample.

The final steps of oligo-poisoning confirmation, separation and detection of PCR amplification products, can be performed by any appropriate methods known in the art. For example, separation of PCR products can be performed according to any methods known in the art capable of separating oligonucleotides of the appropriate length, for example in the case of GeneCalling™ having length of from 50–1000 bp., and is preferably performed by electrophoresis in a denaturing polyacrylamide gel with a gel concentration suitable for the separation of oligonucleotides having such a range of lengths. Detection of separated oligonucleotides can be by any means known in the art, and is preferably by detection of fluorescent emissions stimulated from dye labels conjugated to the primers.

The PCR amplification protocols used in the present invention are designed to have maximum specificity and reproducibility. First, PCR amplification produces fewer unwanted products if the linkers remain substantially melted and unable to initiate DNA strands, such as by performing all amplification steps at a temperature near or above the $T_m$ of the linker. Second, the amplification primers are preferably designed for high amplification specificity by having a high $T_m$, preferably above 50° C. and most preferably above 68° C., to ensure specific hybridization with a minimum of mismatches. In addition, they are further chosen not to hybridize with any native cDNA species to be analyzed. Phasing primers, which are alternatively used for PCR amplification, have similar properties. Third, the PCR temperature profile is preferably designed for specificity and reproducibility.

High annealing temperatures minimize primer mis-hybridizations. Longer extension times reduce PCR bias related to smaller fragments. Longer melting times reduces PCR amplification bias related to high G+C content. A preferred PCR temperature cycles is 95° C. for 30 sec., then 57° C. for 1 min., then 72° C. for 2 min. Fourth, it is preferable to include Betaine in the PCR reaction mix, as this has been found to improve amplification of hard to amplify products. To further reduce bias, large amplification volumes and a minimum number of amplification cycles, typically between 10 and 30 cycles, are preferred. Any other techniques designed to raise specificity, yield, or reproducibility of amplification are applicable to this amplification methodology. For example, one such technique is the use of 7-deaza-2'-dGTP in the PCR reaction in place of dGTP. This nucleotide analog has been shown to increase PCR efficiency for G+C rich targets. See e.g., Mutter, et al., 1995. *Nuc. Acid Res.* 23:1411–1418). Another such technique is the addition of tetramethylammonium chloride to the reaction mixture, which has the effect of raising the $T_m$. See e.g., Chevet, et al., 1995, *Nuc. Acids Res.* 23:3343–3344.

The PCR temperature profile is performed according to the preferred protocol for a certain number of cycles. Following the amplification step, optional cleanup and separation steps prior to length separation and fragment detection can be advantageous to substantially eliminate certain unwanted DNA strands and thereby to improve the signal to noise ratio of GeneCalling™ signals, or to substantially separate the reaction products into various classes and thereby to simplify interpretation of detected fragment patterns by removing signal ambiguities.

For example, unused primer strands and single strands produced by linear amplification are unwanted in later steps. These steps are based upon various types of primer enhancements including conjugated capture moieties and release means.

In one embodiment of these optional primer enhancement steps where one of the two primers used has a conjugated capture moiety, GeneCalling™ reaction products fall into certain categories. These categories (described without limitation in the case where the capture moiety is biotin) include:

(a) dsDNA fragments neither strand of which has a biotin moiety;

(b) dsDNA fragments having only one strand with a conjugated biotin moiety;

(c) dsDNA molecule fragments having biotin moieties conjugated to both strands; and (d) unwanted single-stranded DNA (ssDNA) strands with and without conjugated biotin.

The additional method steps comprise contacting the amplified fragments with streptavidin affixed to a solid support, preferably streptavidin magnetic beads, washing the beads to in a non-denaturing wash buffer to remove unbound DNA, and then resuspending the beads in a denaturing loading buffer and separating the beads from this buffer. The denatured single strands are then passed to the separation and detection steps.

As a results of these steps only the strand of category "b" without biotin is removed in the loading buffer for separation and detection. Thereby, only fragments cut on either end by different REs and freed from single stranded contaminants are separated and detected with minimized noise. Category "a" products are not bound to the beads and are washed away in the non-denaturing wash buffer. Similarly, class "d" products without biotin moieties are washed away. All products with a conjugated biotin are retained by the streptavidin beads after washing. The denaturing loading buffer denatures categories "b" and "c" products attached to the beads, but both strands of category "c" products have conjugated biotin and remain attached to the beads. Similarly, class "d" products with conjugated biotin are retained by the beads.

In another embodiment, the biotinylated primer can include a release means in order to recover fragments of class "c". After the step of suspension in a denaturing buffer, the releasing means (e.g. UDG or AscI) can be applied to release the biotinylated strands for separation and detection. Fragments detected at this second separation in addition to those previously detected then represent class "c" products.

Further embodiments will be apparent to those of skill in the art. For example, two or more types of capture moieties can be used in a single reaction to separate different classes of products. Capture moieties can be combined with release means to achieve similar separation. Label moieties can be combined with capture moieties to verify separations or to run reactions in parallel.

The present invention may also be adapted to other, less preferred, means for single strand separation and product concentration that are known in the art. For example, single strands can be removed by the use of single strand specific exonucleases. Mung Bean exonuclease, Exo I or S1 nuclease can be used, with Exo I preferred because of its higher specificity for single strands while S1 nuclease is least preferred. Other methods to remove unwanted strands include the affinity based methods of gel filtration and affinity column separation. Amplified products can be concentrated by ethanol precipitation or column separation.

The next step in the GeneCalling™ methodology is the separation according to length of the amplified fragments followed by detection the fragment lengths and end labels (if any).

Lengths of the fragments cut from a cDNA sample typically span a range from a few tens of base pairs to perhaps 1000 bp. Any separation method with adequate length resolution, preferably at least to three bp in a 1000 base pair sequence, can be used. It is preferred to use gel electrophoresis in any adequate configuration known in the art. Gel electrophoresis is capable of resolving separate fragments which differ by three or more base pairs and, with knowledge of average fragment composition and with correction of composition induced mobility differences, of achieving a length precision down to 1 bp. A preferable electrophoresis apparatus is an ABI 377 (Applied Biosystems, Inc.) automated sequencer using the Gene Scan software (Applied Biosystems, Inc.) for analysis. The electrophoresis can be done by suspending the reaction products in a loading buffer, which can be non-denaturing, in which the dsDNA remains hybridized and carries the labels (if any) of both primers. The buffer can also be denaturing, in which the dsDNA separates into single strands that typically are expected to migrate together (in the absence of large average differences in strand composition or significant strand secondary structure).

The length distribution is detected with various detection means. If no labels are used, means such as antigen (Ag) and antibody (Ab) staining and intercalating dyes can be used. Here, it can be advantageous to separate reaction products into classes, according to the previously described protocols, in order that each band can be unambiguously identified as to its target end subsequences. In the case of fluorochrome labels, since multiple fluorochrome labels can be typically be resolved from a single band in a gel, the products of one recognition reaction with several REs or other recognition means or of several separate recognition reactions can be analyzed in a single lane. However, where one band reveals signals from multiple fluorochrome labels, interpretation can be ambiguous: is such a band due to one fragment cut with multiple REs or to multiple fragments each cut by one RE. In this case, it can also be advantageous to separate reaction products into classes.

Following detection, the resulting electrophoretic banding patterns and mobilities are utilized to generate an electropherogram. The electropherogram provides a graphical plot of the electrophoretic mobilities of each individual, amplified nucleic acid fragment.

3. Utilization of the Oligo-Poisoning Methodology for Sequence Confirmation of the Human C1r Gene Sequence The application of the oligo-poisoning methodology to the analysis of a RE-generated sequence derived from the Human Complement Component 1, Subcomponent r (c1R) gene will now be discussed.

Human c1R poly(A), mRNA was utilized to generate a homologous cDNA by standard protocols known within the relevant fields. FIG. 4 illustrates the nucleotide sequence of the 2493 c1R cDNA (SEQ ID NO:1). Following synthesis, the c1R cDNA was digested with the REs BspH1 (recognition sequence—TCATA) and EcoR1 (recognition sequence—GAATTC) to produce a 318 bp. fragment. With reference to FIG. 4, the recognition sites for BspH1 and EcoR1 are shown by the underlined sequence; whereas the nucleotide sequence of the 318 bp. fragment generated by the EcoR1- and BspH1-digestion of the c1R cDNA (hereinafter referred to as the "c1R fragment") is shown as bold sequence.

Following RE-digestion, the c1R fragment was isolated and standard PCR amplifications were performed utilizing standard (i.e., non-poisoning) PCR primers, 24 nt. in length, which were complementary to the EcoR1 and BspH1 recognition sites. The two standard primers, defined a J-primer and R-primer, had the following sequences:

J-primer: $_{5'}$-ACC GAC GTC GAC TAT CCA TGA AGA-$_{3'}$ (SEQ ID NO: 2).

R-primer: $_{5'}$-AGC ACT CTC CAG CCT CTC ACC GAA-$_{3'}$ (SEQ ID NO: 3).

Figure 5A:
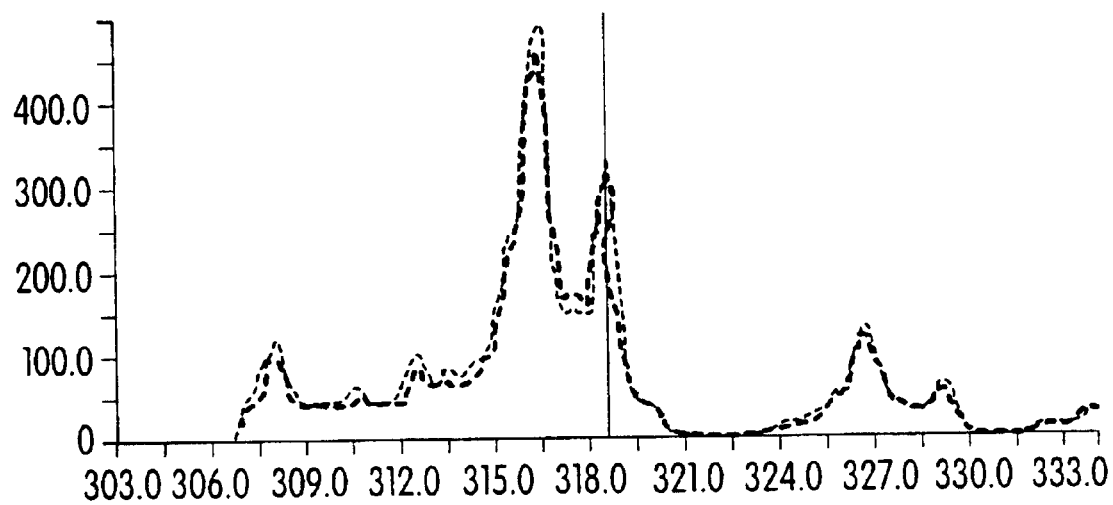
FIG. 5, Panels A & B are electropherograms of the up and down traces generated by GeneCalling™ PCR amplification reactions with the C1r cDNA. These reactions utilized either the "J" primer (complementary to the BspH1 recognition sequence) or "R" primer (complementary to the EcoR1 recognition sequence).
Figure 5B:
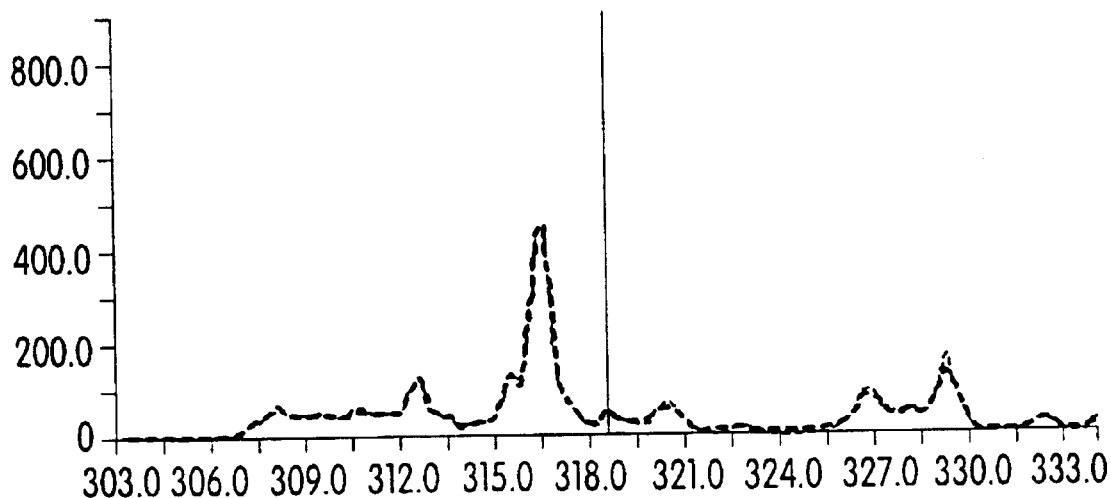

PCR amplifications of the c1R fragment utilizing either the J-primer or R-primer were then performed as disclosed in Section 1 and the amplification products were separated by gel electrophoresis. The electrophoretic banding patterns and mobilities of the amplification products produced by the J-primer PCR reaction and the R-primer PCR reaction were then used to generate electropherograms. FIG. 5, panel A and panel B illustrate the electropherogram results of the "up trace" and "down trace" of the cR1 fragment amplification, respectively. As may be ascertained by examination of FIG. 5, Panels A & B, a nucleic acid fragment having an approximate length of 318.7 bp. was found. In addition, comparison of panel A (up trace) with panel B (down trace) electropherograms, illustrates a marked reduction in the signal intensity of this aforementioned 318.7 bp. fragment. This reduction is indicative of differences in the level of expression of the c1R gene (mRNA).

Next, utilizing the results obtained in the first, PCR amplification reaction (i.e., GeneCalling™), sequence confirmation by the oligo-poisoning methodology of the present invention was performed. Two "poisoning" primers, 22 nt. in length, were generated which possessed sequence which corresponded the last 6 nucleotides of the standard J- and R-primers. The remaining 16 nt. of sequence was designed to correspond to the c1R cDNA sequence. The "poisoning" primers possessed the following nucleotide sequence:

$_{5'}$-TGA AGA CAT GAC CTC AGG TTT G-$_{3'}$ (corresponds to J-primer) (SEQ ID NO: 4)

$_{5'}$-ACC GAA AAT TCT GGG CTC AGT C-$_{3'}$ (corresponds to R-primer) (SEQ ID NO: 5)

PCR amplification was then performed as disclosed in Section 2(b) and the resulting amplification products were separated by gel electrophoresis. As in the initial GeneCalling™ amplification, electropherograms were generated for the amplification reactions utilizing the two "poisoning" primers. FIG. 6, Panels A & B illustrate the electropherograms for the "poisoning" primer corresponding to the J-primer and the "poisoning" primer corresponding to the R-primer, respectively. Comparison of FIG. 6, Panels A & B, demonstrates an approximate 3-fold reduction in the signal corresponding to the 318.7 nt. fragment. Thus, confirming the nucleic acid sequence identity derived from the original GeneCalling™ methodology.

The present invention is not to be limited in scope by the specific embodiments disclosed herein. Indeed, various modifications of the present invention, in addition to those described herein, will become readily apparent to those individuals skilled in the relevant arts from the foregoing descriptions and accompanying figures. Such modifications are intended to fall within the scope of the appended claims.

In addition, various publications are cited herein and their disclosures are hereby incorporated by reference in their entirety.

---

What is claimed is:

1. A method for identifying one or more nucleic acids in a sample comprising a plurality of nucleic acids having different nucleotide sequences, said method comprising:

(a) providing a sample contacted by one or more recognition means, each of said recognition means recognizing a different target nucleotide sequence or different set of target nucleotide subsequences;

(b) generating one or more signals from said sample by amplifying one or more sequences in said sample with at least one amplification means, each generated signal arising from a nucleic acid in said sample and comprising a representation of (i) the size of the sequence comprising said target nucleotide subsequences in said nucleic acid, and (ii) the identities of said target subsequences in said nucleic acid;

(c) searching a nucleotide sequence database for sequences that have a corresponding size and identified target subsequence as one or more of the nucleic acids generating said signal, said database comprising a plurality of known nucleotide sequences of nucleic acids that may be present in the sample, a sequence from said database matching the generated signal when the sequence from said database has both (i) the same size of the sequence comprising said target nucleotide subsequences as is represented by the generated signal, and (ii) the same target subsequences as are represented by the generated signal, or target subsequences that are members of the same sets of target subsequences represented by the generated signal, thereby identifying a putative matching sequence;

(d) contacting under amplifying conditions said sample with said amplification means and one or more poisoning primers to form a reamplified signal corresponding to said putative matching sequence, wherein said poisoning primers are capable of hybridizing to and amplifying only nucleic acids having said putative matching sequence, said poisoning primers being unlabeled or differentially labeled from said amplification means and having a sequence comprising a first subsequence that is a portion of said putative matching sequence and a second subsequence; and (e) comparing the reamplified signal of said putative matching sequence to the signal of said putative matching sequence in step (b), wherein a decrease in the reamplified signal relative to the amplified signal verifies the identity of said matching sequences thereby identifying one or more nucleic acids in said sample.

2. The method of claim 1 wherein at least one of said generated signals corresponds to a sequence having a size and target subsequence of a sequence present in said sequence database.

3. The method of claim 1 wherein the confirming step (d) additionally comprises the steps of:

recovering a fragment of a nucleic acid in the sample which generates said signal;

sequencing said fragment to determine at least a partial sequence for said fragment; and verifying that said sample comprises a nucleic acid having a sequence comprising at least a portion of said determined sequence.

4. The method of claim 1 wherein said plurality of nucleic acids are DNA.

5. The method of claim 4, wherein the [step of probing] contacting comprises:

digesting the sample with one or more restriction endonucleases, said restriction endonucleases having recognition sites that are said target subsequences and leaving single-stranded nucleotide overhangs on the digested ends;

hybridizing double-stranded adapter nucleic acids with the digested sample fragments, said adapter nucleic acids having an end complementary to one of said single-stranded overhangs; and ligating the complementary ends end the of adapter nucleic acids to the complementary 5'-end of a strand of the digested sample fragments to form ligated nucleic acid fragments.

6. The method of claim 1, wherein said poisoning primers are unlabeled.

7. A method of confirming a putatively identified sequence of a nucleic acid fragment in a sample of nucleic acid fragments, wherein each nucleic acid fragment in said sample has ends with known terminal subsequences, said method comprising;

(a) providing an amplified nucleic acid sample comprising an amplified signal associated with said putatively identified sequence, said amplified nucleic acid sample generated by contacting said nucleic acid fragments in said sample in amplifying conditions with a nucleic acid polymerase and at least one amplification means having sequences comprising hybridizable portions of said known terminal subsequence;

(b) contacting said amplified nucleic acid sample in amplifying conditions with a nucleic acid polymerase, said amplification means and poisoning primers to generate a reamplified signal associated with said putatively identified sequence, said poisoning primers having a sequence comprising a first subsequence that is a portion of the sequence of one of said known terminal subsequences and a second subsequence that is a hybridizable portion of said putatively identified sequence that is adjacent to said one known terminal subsequence, wherein nucleic acids amplified with said poisoning primer are distinguishable upon detection from nucleic acids amplified only with said amplification means; and (c) comparing said reamplified signal with said amplified signal, wherein a decrease in the amplified signal relative to said reamplified signal confirms the identity of said putatively identified sequence.

8. The method of claim 7 wherein said poisoning primers are labeled such that they are distinguishable from said amplification means.

9. The method of claim 7 wherein said poisoning primers are unlabeled.

10. The method of claim 9 further comprising before step (a) the steps of:

contacting said nucleic acid fragments in said sample in amplifying conditions with a nucleic acid polymerase and said amplification means to form said amplified nucleic acid sample;

separating the amplified nucleic acid sample; and detecting said separated products.

11. The method of claim 7 wherein said sample of nucleic acids is produced according to steps (a) and (b) of claim 1.

12. The method of claim 9 wherein said sample of nucleic acids is produced according to steps (a) and (b) of claim 1.

13. The method of claim 7 wherein said sample of nucleic acids is produced according to a method comprising:

synthesizing cDNA from mRNA using a method comprising contacting said mRNA with a first-strand primer comprising one or more phasing nucleotides and a first non-complementary heel subsequence;

digesting said cDNA into fragments with a restriction endonuclease;

ligating to said fragments a partially double stranded second primer comprising at its 5' terminus a subsequence that is not complementary to said digested cDNA; and amplifying said ligated fragments by contacting them with a DNA polymerase and a first amplifying primer comprising at least a portion of said first non-complementary heel subsequence and a second amplifying primer comprising at least a portion of said second 5' non-complementary subsequence.

14. The method of claim 7 wherein said sample of nucleic acids is produced according to a method comprising:

synthesizing first cDNA from mRNA using a method comprising contacting said mRNA with a first first-strand primer comprising one or more phasing nucleotides and a recognition site for a rare-cutting restriction endonuclease;

digesting said first cDNA with said rare-cutting restriction endonuclease and a second restriction endonuclease;

ligating said digested first cDNA into a cloning vector in an anti-sense orientation; synthesizing cRNA from said cloning vector;

synthesizing second cDNA from said cRNA using a method comprising contacting said cRNA with a second first-strand primer comprising one or more phasing nucleotides and a subsequence of said cloning vector adjacent to the 3'-end of said ligated first cDNA; and amplifying said second cDNA by contacting said second cDNA with a DNA polymerase and a first amplifying primer comprising a subsequence of said cloning vector adjacent to the 3'-end of said ligated first cDNA and a second amplifying primer comprising a subsequence of said cloning vector adjacent to the 5'-end of said ligated first cDNA.

\* \* \* \* \*